US012709776B2

(12) United States Patent
Igarashi et al.

(10) Patent No.: US 12,709,776 B2
(45) Date of Patent: Aug. 18, 2026

(54) MARKER OF EPITHELIAL-MESENCHYMAL TRANSITION IN PANCREATIC CANCER

(71) Applicant: TOHOKU UNIVERSITY, Miyagi (JP)

(72) Inventors: Kazuhiko Igarashi, Miyagi (JP); Mitsuyo Matsumoto, Miyagi (JP); Masaki Sato, Miyagi (JP); Hironari Nishizawa, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 1217 days.

(21) Appl. No.: 17/432,680

(22) PCT Filed: Feb. 22, 2019

(86) PCT No.: PCT/JP2019/006886
§ 371 (c)(1),
(2) Date: Aug. 20, 2021

(87) PCT Pub. No.: WO2020/170446
PCT Pub. Date: Aug. 27, 2020

(65) Prior Publication Data

US 2022/0170106 A1 Jun. 2, 2022

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS 10,888,569 B1 * 1/2021 Rosner .................... A61P 35/00
2012/0282597 A1 11/2012 Sun et al.
2016/0078167 A1 3/2016 Rosner et al.

FOREIGN PATENT DOCUMENTS

JP 2006-304716 11/2006
JP 2009-254364 11/2009
JP 2015-167521 9/2015
WO 2012/149014 11/2012

OTHER PUBLICATIONS

Enard et al. (Science 2002 vol. 296 p. 340) (Year: 2002).*
Cobb et al (Crit Care Med 2002 vol. 30 p. 2711) (Year: 2002).*
International Search Report issued May 21, 2019 in corresponding International (PCT) Patent Application No. PCT/JP2019/006886.
Huang, X. et al., "Functional role of BTB and CNC Homology 1 gene in pancreatic cancer and its association with survival in patients treated with gemcitabine", 2018, Theranostics, vol. 8, issue 12, pp. 3366-3379.
Fujioka, S. et al., "Clinicopathological Investigation of Tumor Angiogenesis and p53 Protein Expression in Tubular Adenocarcinoma of the Pancreas", 2001, Jpn J Gastroenterol Surg., vol. 34, No. 2, pp. 83-90 with partial English translation.
Bernardo, G.M. et al., "FOXA1: a transcription factor with parallel functions in development and cancer", 2012, Biosci. Rep., vol. 32, No. 2, pp. 113-130.
Liang, Y. et al., "Transcriptional Network Analysis Identifies BACH1 as a Master Regulator of Breast Cancer Bone Metastasis", 2012, Journal of Biological Chemistry, vol. 287, No. 40, pp. 33533-33544.
Igarashi, K. et al., "BACH transcription factors in innate and adaptive immunity", 2017, Nature Reviews Immunology, vol. 17, pp. 437-450.
Dohi, Y. et al., "Bach1 inhibits oxidative stress-induced cellular senescence by impeding p53 function on chromatin", 2008, Nat Structural Molecular Biology, vol. 15, No. 12, pp. 1246-1254.
Nakanome, A. et al., "Bach 1 is critical for the transformation of mouse embryonic fibroblasts by $Ras^{V12}$ and maintains ERK signaling", 2013, Oncogene, vol. 32, pp. 3231-3245.
Fang, M. et al., "Common BRAF(V600E)-directed pathway mediates widespread epigenetic silencing in colorectal cancer and melanoma", 2016, PNAS, vol. 113, No. 5, pp. 1250-1255.
Extended European Search Report issued Sep. 29, 2022 in corresponding European Patent Application No. 19916125.8.
Sato, Masaki et al., "BACH1 Promotes Pancreatic Cancer Metastasis by Repressing Epithelial Genes and Enhancing Epithelial-Mesenchymal Transition", Cancer Research, 2020, vol. 80, pp. 1279-1292.
Shajari, Neda et al., "Silencing of BACH1 inhibits invasion and migration of prostate cancer cells by altering metastasis-related gene expression", Artificial Cells, Nanomedicine, and Biotechnology, 2018, vol. 46, No. 7, pp. 1495-1504.
Greither, Thomas et al., "Elevated expression of microRNAs 155, 203, 210 and 222 in pancreatic tumors is associated with poorer survival", International Journal of Cancer, 2010, vol. 126, pp. 73-80.
Li, Chunhe et al., "A landscape view on the interplay between EMT and cancer metastasis", npj Systems Biology and Applications, 2018, vol. 4, No. 34, pp. 1-9.
Chen, Fei et al., "Inherited pancreatic cancer", Chinese Clinical Oncology, 2017, vol. 6, No. 6:58, pp. 1-16.
Davudian Sadaf et al., "BACH1, the master regulator gene: A novel candidate target for cancer therapy", Gene, 2016, vol. 588, pp. 30-37.

(Continued)

*Primary Examiner* — Katherine D Salmon
(74) *Attorney, Agent, or Firm* — Wenderoth, Lind & Ponack, L.L.P.

(57) ABSTRACT

In order to elucidate the mechanism of malignant alteration of pancreatic cancer caused by BACH1, changes in the gene expression depending on the expression level of BACH1 in the pancreatic cancer cell line were clarified by RNA sequencing. As a result of experiments on in vitro migration ability and invasion ability and in vivo orthotopic transplantation, BACH1 was found to be used as an excellent biomarker for epithelial-to-mesenchymal transition of pancreatic cancer when used alone or in combination with its downstream regulator FOXA1.

2 Claims, 7 Drawing Sheets

Specification includes a Sequence Listing.

(56) References Cited

OTHER PUBLICATIONS

Roe, Jae-Seok et al., "Enhancer Reprogramming Promotes Pancreatic Cancer Metastasis", Cell, 2017, vol. 170, No. 5, pp. 875-888.
Zhang, Xinyue et al., "Bach1: Function, Regulation, and Involvement in Disease", Oxidative Medicine and Cellular Longevity, 2018, vol. 2018, Article ID 1347969, pp. 1-8.

* cited by examiner

| interaction | P |
|---|---|
| A-B | 0.2416 |
| A-C | 0.0318 |
| A-D | 0.4265 |
| B-C | <0.0001 |
| B-D | 0.0003 |
| C-D | 0.00114 |

MARKER OF EPITHELIAL-MESENCHYMAL TRANSITION IN PANCREATIC CANCER

TECHNICAL FIELD

The present invention relates to a method of evaluating epithelial-to-mesenchymal transition ability of pancreatic cancer, a method of evaluating metastasis ability or invasion ability of pancreatic cancer, a method of predicting prognosis of pancreatic cancer, a pancreatic cancer metastasis suppressant, and a method of screening for a pancreatic cancer metastasis suppressant.

BACKGROUND ART

Pancreatic cancer is a cancer that mainly develops in the epithelium of the pancreatic duct, and has the poorest prognosis with a 5-year survival rate of 10% or less after diagnosis. Surgical resection is the only therapy that can be expected to cure pancreatic cancer. However, early detection of pancreatic cancer is difficult, 80% of cases are inoperable at the time of diagnosis, and due to its high malignancy, chemotherapy is poorly effective. Thus, there are currently few effective diagnostic and therapeutic methods.

The mechanism of pancreatic cancer development is well understood, and since the 1950s, a multistage carcinogenesis hypothesis has been considered from pathological observation of lesions. Recent powerful genome mutation analysis reveals the accumulation of mutant genes corresponding to the carcinogenic process of pancreatic cancer. At present, the multistage carcinogenesis theory (genetic progression model) that carcinogenesis is caused by the accumulation of mutant genes is accepted. Mutations found early in precancerous lesions during the carcinogenic process include mutations in the KRAS gene, and at least 90% cases of pancreatic cancer are known to have KRAS mutations. KRAS is usually activated by binding of GTP as an external stimulus response to the receptor-type tyrosine kinase receptor, and promotes the RAS/RAF/MEK/ERK signaling pathway so as to cause cell responses such as cell proliferation, apoptosis, and differentiation. Its activity is terminated when GTP is hydrolyzed to GDP. However, many of the KRAS gene mutations found in cancers inhibit the hydrolysis of GTP and remain in an activated state at all times, promoting the growth and malignant alteration of cancer cells. This activated RAS mutation is found in about 30% of all human cancers other than pancreatic cancer. Therefore, although research on RAS-targeted inhibitors such as competitive inhibitors of RAS and GTP has been energetically promoted so far, sufficient effects have not been obtained due to the presence of GTP and GDP at high concentrations in cells, and none of such inhibitors has been clinically applied.

Therefore, further elucidation of the mechanism of malignant alteration of pancreatic cancer is important, but gene mutations specific to metastasis and recurrence have not yet been identified. In addition, changes in gene expression and signal transduction in primary tumors in the acquisition of metastasis ability, and as metastasis-promoting factors, not only self-replication of cancer cells and epithelial-to-mesenchymal transition, but also the influence of the surrounding environment of cancer are considered. However, there are still many unclear points.

BACH1 (BTB and CNC homology 1) suppresses gene expression such as heme oxygenase-1 (HO-1), which reduces oxidative stress under normal conditions, and contributes to the maintenance of cell homeostasis by suppressing the increase of reactive oxygen species (ROS) when being excreted from the nucleus under oxidative stress (Non Patent Literature 1). In addition, BACH1 suppresses the expression of part of its target gene by forming a complex with the tumor suppressor transcription factor p53, and suppresses cell aging (Non Patent Literature 2). In an experiment in which mutant Ras-transfected mouse embryonic fibroblasts (MEFs) were subcutaneously transplanted into mice, tumor formation and growth are significantly inhibited with Bach1-deficient MEFs, compared to wild-type MEFs (Non Patent Literature 3). Regarding the relationship between BACH1 and cancer, it has been reported that BACH1 promotes CpG island methylation and suppresses the expression of tumor suppressor genes in colorectal cancer and malignant melanoma with BRAF mutations (Non Patent Literature 4). It has also been reported that in breast cancer, BACH1 promotes bone metastasis by controlling the expression of a plurality of genes related to metastasis (Non Patent Literature 5).

CITATION LIST

Non Patent Literature

Non Patent Literature 1: Nat Rev Immunol, 2017. 17(7): p. 437-450

Non Patent Literature 2: Nat Struct Mol Biol. 2008. 15(12): p. 1246-54

Non Patent Literature 3: Oncogene, 2013. 32(27): p. 3231-45

Non Patent Literature 4: Proc Natd Acad Sci USA. 2016. 113(5): p. 1250-5

Non Patent Literature 5: J Biol Chem, 2012. 287(40): p. 33533-44

SUMMARY OF INVENTION

Technical Problem

An object of the present invention is to provide a novel epithelial-to-mesenchymal transition marker of pancreatic cancer, a pancreatic cancer metastasis or invasion marker, a pancreatic cancer prognosis marker, a pancreatic cancer metastasis suppressant, and a method of screening for a pancreatic cancer metastasis suppressant.

Solution to Problem

The present inventors focused on BACH1 and investigated the relationship between BACH1 expression and the prognosis of pancreatic cancer using the database of The Cancer Genome Atlas (TCGA), thereby obtaining the results showing significantly poorer prognosis in pancreatic cancer with high BACH1 expression. From these findings, it was considered that BACH1 contributed to the malignant alteration of pancreatic cancer. Furthermore, the results of immunostaining of BACH1 in human pancreatic cancer tissue specimens also confirmed the worsened prognosis with high BACH1 expression.

Therefore, in this study, in order to elucidate the mechanism of malignant alteration of pancreatic cancer caused by BACH1, changes in the gene expression depending on the expression level of BACH1 in the pancreatic cancer cell line were clarified by RNA sequencing. Focusing on epithelial-to-mesenchymal transition, the present inventors conducted experiments on in vitro migration ability and invasion ability and in vivo orthotopic transplantation. In addition, it was shown that BACH1 can be used as an excellent biomarker for epithelial-to-mesenchymal transition of pancreatic cancer, an excellent biomarker for metastasis or invasion of pancreatic cancer, and an excellent biomarker for predicting the prognosis of pancreatic cancer in combination with its downstream regulator.

Furthermore, it was shown that pancreatic cancer metastasis can be suppressed by controlling the expression of metastasis-related genes by BACH1, and a method of screening a drug that can suppress pancreatic cancer metastasis was shown.

The present invention has been completed based on the findings as described above.

Specifically, the present invention is as follows.

[1] A (data acquisition) method of evaluating epithelial-to-mesenchymal transition ability of pancreatic cancer in vitro, the method comprising a step of measuring an expression level of BACH1.

[2] The (data acquisition) method of evaluating epithelial-to-mesenchymal transition ability of pancreatic cancer in vitro according to [1], the method further comprising a step of measuring an expression level of FOXA1.

[3] A (data acquisition) method of evaluating metastasis ability or invasion ability of pancreatic cancer in vitro, the method comprising a step of measuring an expression level of BACH1.

[4] The (data acquisition) method of evaluating metastasis ability and invasion ability of pancreatic cancer in vitro according to [3], the method further comprising a step of measuring an expression level of FOXA1.

[5] A (data acquisition) method of predicting prognosis of pancreatic cancer in vitro, the method comprising a step of measuring an expression level of BACH1.

[6] The (data acquisition) method of predicting prognosis of pancreatic cancer in vitro according to [5], the method further comprising a step of measuring an expression level of FOXA1.

[7] A method of screening for a pancreatic cancer metastasis suppressant, comprising: a step of adding a drug candidate substance to cells expressing a BACH1 gene or a reporter gene linked to a promoter of the BACH1 gene; a step of measuring an expression level of the BACH1 gene or reporter gene; and a step of selecting a substance for reducing the expression level.

[8] A pancreatic cancer metastasis suppressant, containing, as an active ingredient, a drug for reducing BACH1 gene expression.

[9] The pancreatic cancer metastasis suppressant according to [8], which inhibits epithelial-to-mesenchymal transition ability of pancreatic cancer cell.

[10] The pancreatic cancer metastasis suppressant according to [8] or [9], wherein the drug is siRNA for a BACH1 gene.

Advantageous Effects of Invention

According to the present invention, it is possible to obtain data for evaluating epithelial-to-mesenchymal transition ability of pancreatic cancer, data for evaluating metastasis ability or invasion ability of pancreatic cancer, and data for predicting prognosis of pancreatic cancer, thereby making it possible to diagnose the prognosis of pancreatic cancer. Further, according to the present invention, it is possible to provide a pancreatic cancer metastasis suppressant and screen for a pancreatic cancer metastasis suppressant.

Typical microscopic images of scratch assay and column diagrams of measured cell mobility are shown: (A) BACH1 knockdown (siBACH1) AsPC1 cells and their control cells (siCont.); and (B) BACH1-overexpressing (exBACH1) Panc1 cells and their control cells (EV). (C) Representative microscopic images of transwell assay and invasion assay of BACH1 knockdown AsPC1 and SW1990 and the number of migrated or invaded cells as a column diagram are shown. Each experiment was performed three times or more independently. In the column diagram, the values for each experiment are shown as dots, the average value is shown as a column, and the standard error is shown as a bar. The statistically significant difference was tested by the Student's t-test. The P value is shown (*: $P<0.05$, **: $P<0.01$).

Figure 5:
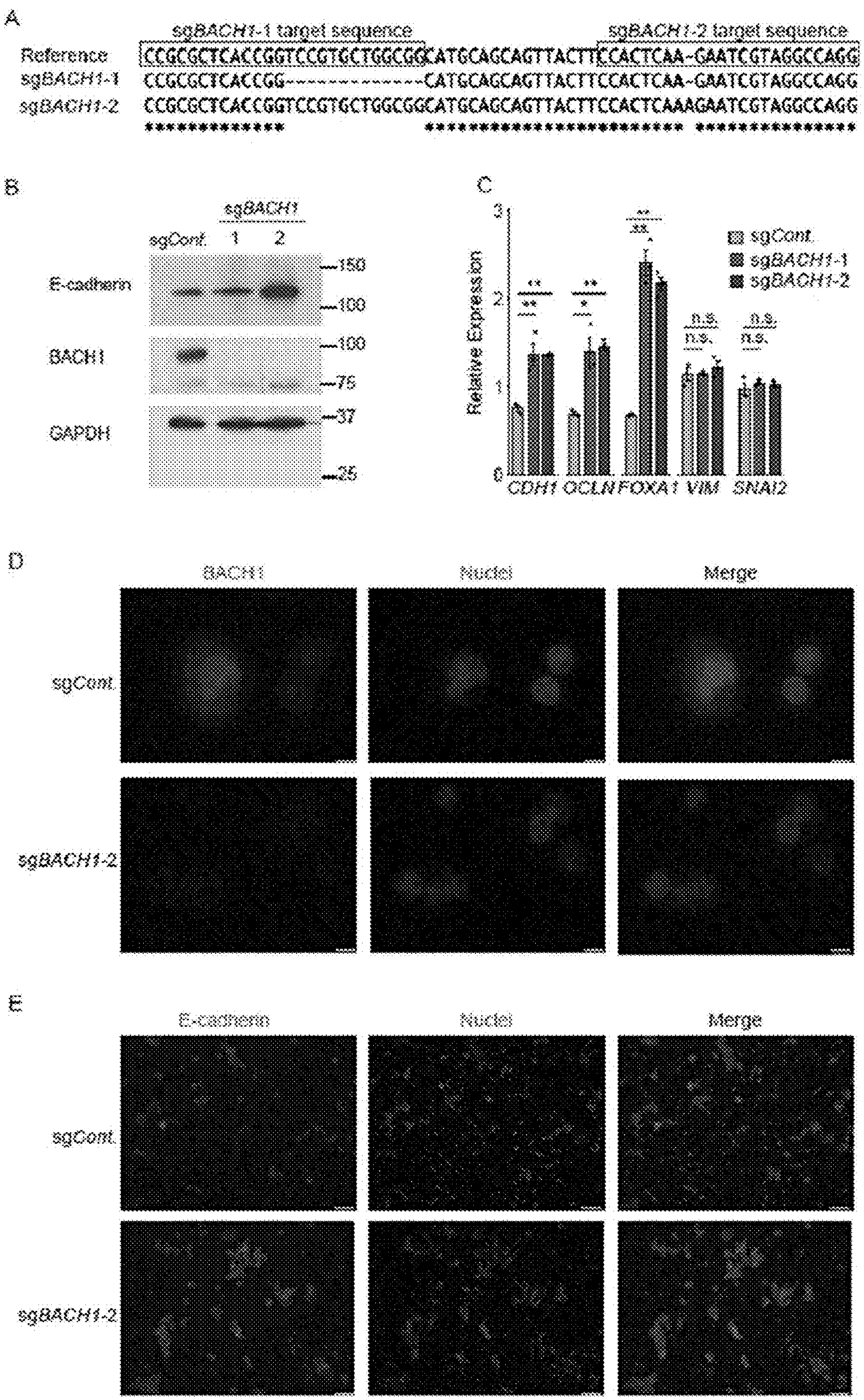

FIG. 5 shows the establishment of BACH1 knockout AsPC1 cell lines. (A) DNA sequencing results at target sites of each of the clones (sgBACH1-1 and sgBA(CH1-2) established from two types of guide RNA are shown. The two guide RNAs were designed with the exon 2 internal sequence of the BACH1 gene as the target, sgBACH1-1 for 13 bp base deletion mutation and sgBACH1-2 for single-base insertion mutation. As the reference sequence, hg19, which is the human reference genome, was used. (B) Western blot images (photographs) of BACH1, E-cadherin, and GAPDH as the as an internal standard in BACH1knockout (sgBACH1) AsPC1 cells and their control cells (sgCont.) are shown. (C) The RT-qPCR results for BACH1 knockout AsPC1 are shown. The mRNA expression level of each factor was corrected by the ACTB mRNA expression level. Each experiment was performed three times independently. The values for each experiment are shown as dots, the average value is shown as a column, and the standard error is shown as a bar. The statistically significant difference was tested by the Student's t-test. The P value is shown (*: $P<0.05$, **: $P<0.01$, n.s.: not significant). Immunofluorescent staining images of BACH1 knockout AsPC1 constructed using guide RNA sgBACH1-2 are shown: (D) BACH1; and (E) E-cadherin. The scales represent 7.5 μm and 75 μm, respectively.

Figure 6:
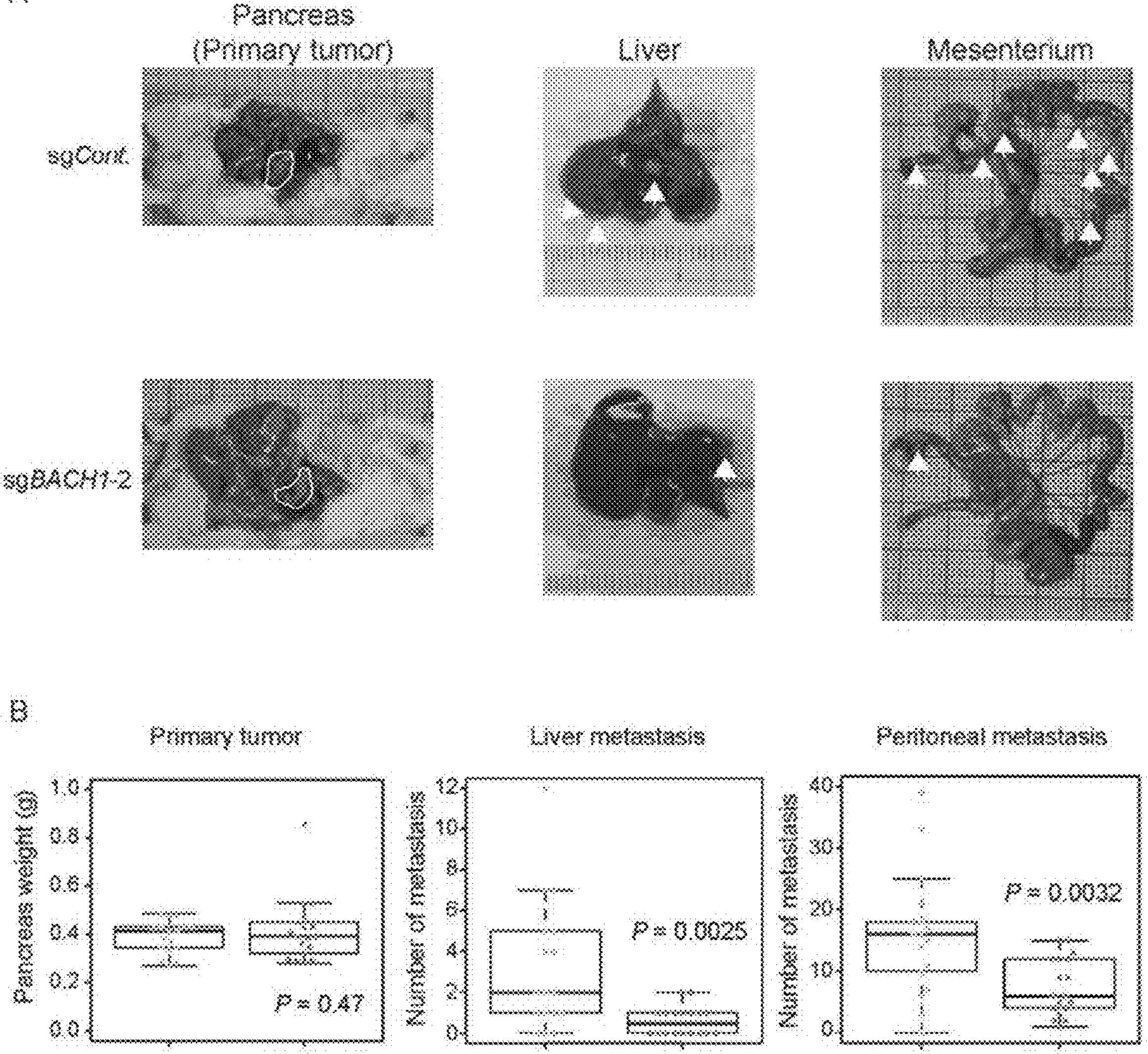

FIG. 6 shows that BACH1 promotes metastasis in vivo but does not affect tumorigenesis. (A) Typical examples of pancreatic tumors, liver metastases, and mesenteric dissemination 5 weeks after the implantation of BACH1 knockout (sgBACH1-2) AsPC1 cells or their control cells (sgCont.) in the pancreas of each of NOG mice (BACH1 wild-type AsPC1: n=17; BACH1 knockout AsPC1: n=18) are shown. Each area surrounded by the white line indicates a tumor formed in the pancreas, and each white arrow indicates a metastatic lesion. (B) The weight of the removed pancreas, the number of liver metastases, and the number of peritoneal metastases are shown as box plots. The bottom of each box shows 25% of the data, the top of the same shows 75%, the middle line of the same shows the median, and the whiskers show the maximum and minimum values, respectively. The statistically significant difference was tested by the Student's t-test. The P value was calculated.

Figure 7:
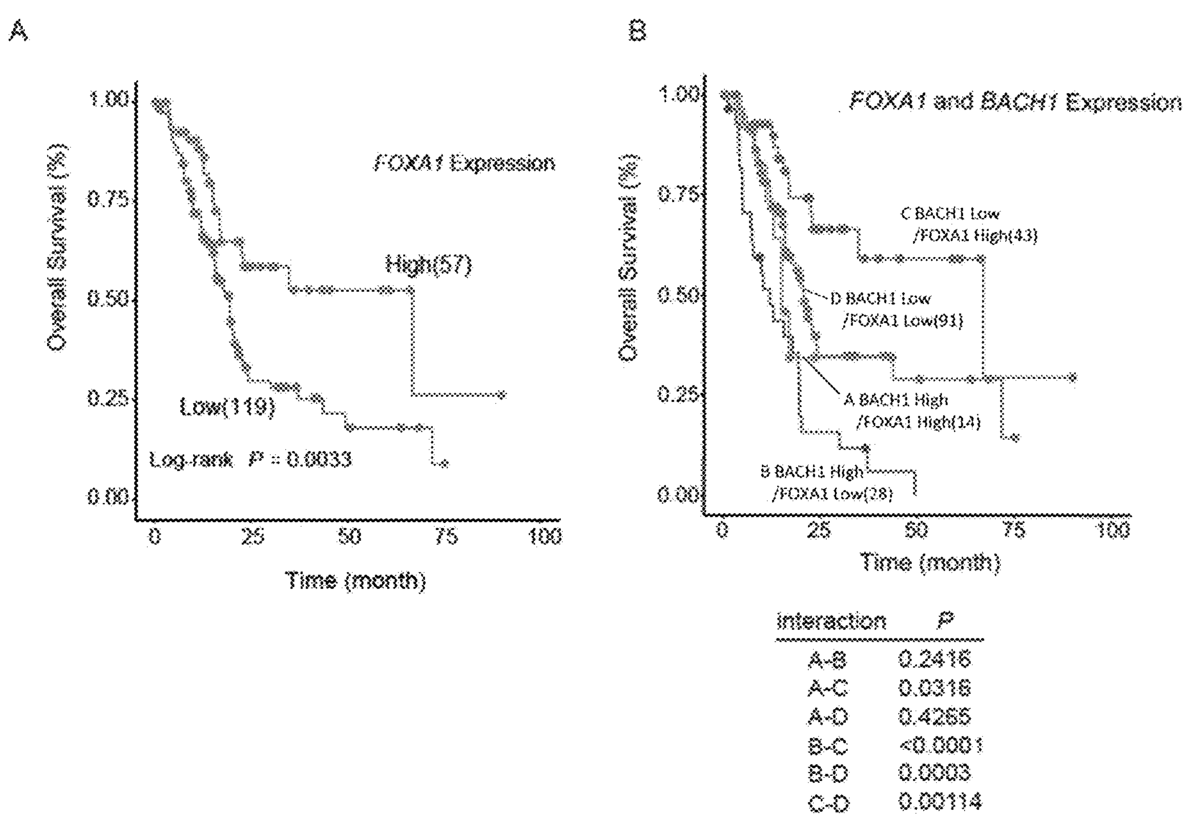

FIG. 7 shows that BACH1 becomes a more accurate prognostic marker for pancreatic cancer with the addition of functional evaluation thereof. The RNA sequence data of 176 specimens obtained from the TCGA database were classified into two or four groups by the cutoff value obtained from the ROC curve based on the expression levels: (A) FOXA1; and (B) BACH1 and FOXA1. Overall survival was analyzed by the Kaplan-Meier method among the classified groups. The statistically significant difference was tested by the log-rank test. The P value is shown.

DESCRIPTION OF EMBODIMENTS

<Method of Evaluating Epithelial-to-Mesenchymal Transition Ability of Pancreatic Cancer>

The present invention provides a (data acquisition) method of evaluating epithelial-to-mesenchymal transition ability of pancreatic cancer in vitro, the method comprising a step of measuring an expression level of BACH1.

The BACH1 gene may be a gene from a test subject, and specifically, genes containing the base sequences shown below are exemplified.

As the base sequence of BACH1 gene, the base sequence set forth in SEQ ID NO: 1 is exemplified in a case in which a test subject is a human. In addition, the BACH1 gene includes DNA that hybridizes with DNA having a complementary sequence of the base sequence set forth in SEQ ID NO: 1 under stringent conditions as long as it encodes a protein having a function as a transcription factor. Here, examples of the stringent condition include washing under the conditions of 0.1×SDS, 0.1×SSC, and 68° C. In a case in which a different animal is used as a test subject, the homolog gene from the animal is the measurement target.

The BACH1 protein is not limited as long as it is a protein from a test subject, and specific examples thereof include proteins containing the amino acid sequences shown below. In addition, the BACH1 protein also encompasses protein fragments, analogs, and variants that have similar associations with pancreatic cancer as in the protein.

As the amino acid sequence of the BACH1 protein, the amino acid sequence set forth in SEQ ID NO: 2 is exemplified in a case in which the test subject is a human. Further, as long as it is a protein having a function as a transcription factor, it may be a protein having an amino acid sequence in which one or several (for example, from 1 to 20) amino acids are substituted, deleted, inserted, or added in this amino acid sequence. In a case in which a different animal is used as a test subject, the homolog protein from the animal is the measurement target.

The present invention may further include a step of measuring the expression level of an epithelial cell marker.

Examples of the epithelial cell marker include FOXA1 (Forkhead Box Protein A1), OCLN (Occludin), PKP2 (Plakophilin 2), CLDN3 (Claudin 3), and CLDN4 (Claudin 4). The epithelial cell marker is preferably FOXAL.

The step may be a step of measuring the expression level of one epithelial cell marker selected from the group consisting of these epithelial cell markers or a step of measuring the expression levels of these two or more epithelial cell markers.

As the base sequence of FOXA1, the base sequence set forth in SEQ ID NO: 3 is exemplified in a case in which a test subject is a human. In addition, the FOXA1 gene includes DNA that hybridizes with DNA having a complementary sequence of the base sequence set forth in SEQ ID NO: 3 under stringent conditions as long as it encodes a protein having a function as a transcription factor. Here, examples of the stringent condition include washing under the conditions of 0.1×SDS, 0.1×SSC, and 68° C. In a case in which a different animal is used as a test subject, the homolog gene from the animal is the measurement target.

As the amino acid sequence of the FOXA1 protein, the amino acid sequence set forth in SEQ ID NO: 4 is exemplified in a case in which the test subject is a human. Further, as long as it is a protein having a function as a transcription factor, it may be a protein having an amino acid sequence in which one or several (for example, from 1 to 20) amino acids are substituted, deleted, inserted, or added in this amino acid sequence. In a case in which a different animal is used as a test subject, the homolog protein from the animal is the measurement target.

Measuring the expression levels of BACH1 and FOXA1 is not particularly limited, but it may be, for example, measuring the expression levels of these mRNAs or proteins.

The expression levels of BACH1 and FOXA1 genes can be measured by, for example, a quantitative PCR method, an RT-PCR method, a quantitative RT-PCR method, a microarray method, a high-throughput sequencing method, a Northern blot method, a spectrophotometric method, or a fluorometric method. In addition, the expression levels of BACH1 and FOXA1 proteins can be measured by, for example, flow cytometry, Western blotting, ELISA, and other immunochemical methods.

Primers, probes, and the like for gene expression analysis can be designed or obtained by using the sequence set forth in SEQ ID NO: 1 or SEQ ID NO: 3, which is the base sequence of the coding region of the BACH1 gene or the FOXA1 gene. The base sequence may be a sequence having 90% or more, preferably 95% or more, more preferably 98% or more identity with the base sequence set forth in SEQ ID NO: 1 or SEQ ID NO: 3. Further, the primers, probes, and the like may be those having 90% or more, preferably 95% or more, more preferably 98% or more identity with the complementary sequence of the base sequence as long as they can specifically bind to the base sequence.

The quantitative PCR method can be carried out by a conventional method without limitation, but a method using an intercalator or a method using a fluorescently labeled probe can be carried out. For example, SYBR (registered trademark) Green I can be used as an intercalator.

As an antibody used for measuring the expression level of the BACH1 protein or FOXA1 protein, a commercially available antibody may be used, or an antibody prepared by using a part of the amino acid sequence of the BACH1 protein or FOXA1 protein set forth in SEQ ID NO: 2 or SEQ ID NO: 4 as an antigen may also be used. The amino acid sequence may be a sequence having 90% or more, preferably 95% or more, more preferably 98% or more identity with the amino acid sequence set forth in SEQ ID NO: 2 or SEQ ID NO: 4. Further, the antibody and the like may be those having 90% or more, preferably 95% or more, more preferably 98% or more identity with the complementary sequence of the amino acid sequence as long as they can specifically bind to the amino acid sequence.

The antibody may be either a monoclonal antibody or a polyclonal antibody, but is preferably a monoclonal antibody in order to stably supply an antibody of stable quality. It may be a fragment of a monoclonal antibody such as Fab' or F(ab')2.

In addition, each antibody that can be used may be from commonly used mice, rats, rabbits, goats, sheep, birds, and the like, but is not limited thereto, and any antibody can be used as long as it is an antibody that specifically binds to the BACH1 protein or FOXA1 protein. The antibody may be labeled, or a labeled secondary antibody may be used.

In the case of using a labeled secondary antibody, it can be used without particular limitation as long as it recognizes a primary antibody. For example, in a case in which the primary antibody is a rabbit antibody, a labeled anti-rabbit IgG antibody can be used as the secondary antibody, and in a case in which the primary antibody is a mouse antibody, a labeled anti-mouse IgG antibody can be used as the secondary antibody.

Examples of a labeling substance include enzymes, radioisotopes, fluorescent substances, luminescent substances, and gold colloid.

Of these, enzymes are preferable from the viewpoints of sensitivity and ease of operation, and peroxidase (PO), horseradish peroxidase (HRP), alkaline phosphatase (AP), lucose oxidase (GOD), and the like are more preferable. In the case of using HRP as a labeling substance, TMB (3,3',5,5'-tetramethylbenzidine) or the like can be used as a substrate, and in the case of using AP as a labeling substance, AMPPD (3-(2'-spiroadamantane)-4-methoxy-4-(3"-phosphoryloxy)phenyl-1,2-dioxetane disodium salt), 9-(4-chlorophenyl thiophosphoryl oxymethylidene)-10-methylacridan disodium salt, or the like can be used as a substrate. In addition to the above, fluorescent dyes such as FITC (fluorescein isothiocyanate) and rhodamine may also be used as a labeling substance.

The method of detecting/quantifying a substance to be measured differs depending on the labeling method, and can be performed by a method well known to those skilled in the art and is not particularly limited. For example, in the case of using PO, HRP, AP, GOD, or the like as a labeling substance, by adding a colorimetric substrate or a luminescent substrate, changes in absorbance and luminescence intensity can be measured to quantify the substance to be measured. In the case of using a fluorescent substance as a labeling substance, the substance to be measured can be quantified by measuring the fluorescence intensity thereof. In the case of using a radioisotope as a labeling substance, the substance to be measured can be quantified by measuring the radioactivity. In the case of using gold colloid as a labeling substance, the substance to be measured can be quantified by measuring the absorbance.

For quantification, for example, it is possible to prepare a calibration curve (standard curve) with a sample of a known concentration in advance and compare the measured value with the calibration curve so as to calculate the expression level of BACH1 protein or FOXA1 protein in the sample.

The concentration of the antibody solution is not particularly limited as long as it does not interfere with the antigen-antibody reaction and is not excessively low with respect to the expression level of BACH1 protein or FOXA1 protein in the sample.

In the present invention, the time for performing the antigen-antibody reaction, the temperature at which the method of the present invention is carried out, the composition, pH, and the like of the diluted solution and washing solution of the sample and reagent are not particularly limited, and conditions that are applied to a commonly used method for quantifying proteins may be sufficient.

The test subject is not particularly limited as long as it is a mammal that expresses BACH1, but a human is preferable.

The target sample to be measured is, for example, a biological sample obtained from a test subject or a healthy subject.

The biological sample may be, for example, cells or tissues of the pancreas, cells or tissues around the pancreas, cells or tissues of any other site where pancreatic cancer may metastasize, or the like. Further, the biological sample may be a body fluid such as blood or lymph that can contain pancreatic cancer cells, or may be circulating cancer cells in blood. The circulating cancer cells in blood are not particularly limited, but can be recovered by, for example, allowing magnetic beads coated with an antibody that recognizes pancreatic cancer to act on the blood and making a positive selection by magnetism.

Epithelial-to-mesenchymal transition means the transformation of epithelial cells into mesenchymal-like cells with migration ability by losing their cell adhesion ability.

The epithelial-to-mesenchymal transition ability can be evaluated by, for example, the following method. The cutoff value of the BACH1 expression level is calculated from the receiver operating characteristic (ROC) curve created using clinical data of pancreatic cancer clinical specimens obtained from the database of the Cancer Genome Atlas (TCGA). In a case in which the expression level of BACH1 in the biological sample obtained from the test subject has exceeded the cutoff value, pancreatic cancer can be evaluated as having high epithelial-to-mesenchymal transition ability, while in a case in which it is not more than the cutoff value, pancreatic cancer can be evaluated as having low epithelial-to-mesenchymal transition ability.

Further, in combination with the expression level of FOXA1, which is an epithelial cell marker, the epithelial-to-mesenchymal transition ability of pancreatic cancer can be evaluated more accurately. As with BACH1, the cutoff value of the FOXA1 expression level is calculated from the receiver operating characteristic (ROC) curve created using clinical data of pancreatic cancer clinical specimens obtained from the database of TCGA. In a case in which the expression level of FOXA1 in the biological sample obtained from the test subject has exceeded the cutoff value and the expression level of BACH1 is not more than the cutoff value, pancreatic cancer can be evaluated as having low epithelial-to-mesenchymal transition ability. Meanwhile, in a case in which the expression level of FOXA1 in the biological sample obtained from the test subject is not more than the cutoff value and the expression level of BACH1 has exceeded the cutoff value, pancreatic cancer can be evaluated as having high epithelial-to-mesenchymal transition ability.

<Method of Evaluating Metastasis Ability or Invasion Ability of Pancreatic Cancer>

The present invention provides a (data acquisition) method of evaluating metastasis ability or invasion ability of pancreatic cancer in vitro, the method comprising a step of measuring an expression level of BACH1.

The metastasis ability or invasion ability of pancreatic cancer can be evaluated by, for example, the following method. The cutoff value of the BACH1 expression level is calculated from the receiver operating characteristic (ROC) curve created using clinical data of pancreatic cancer clinical specimens obtained from the database of the Cancer Genome Atlas (TCGA). In a case in which the expression level of BACH1 in the biological sample obtained from the test subject has exceeded the cutoff value, pancreatic cancer can be evaluated as having high metastasis ability or invasion ability, while in a case in which it is not more than the cutoff value, pancreatic cancer can be evaluated as having low metastasis ability or invasion ability.

Further, in combination with the expression level of FOXA1, which is an epithelial cell marker, the metastasis ability or invasion ability of pancreatic cancer can be evaluated more accurately. As with BACH1, the cutoff value of the FOXA1 expression level is calculated from the receiver operating characteristic (ROC) curve created using clinical data of pancreatic cancer clinical specimens obtained from the database of TCGA. In a case in which the expression level of FOXA1 in the biological sample obtained from the test subject has exceeded the cutoff value and the expression level of BACH1 is not more than the cutoff value, pancreatic cancer can be evaluated as having low metastasis ability or invasion ability. Meanwhile, in a case in which the expression level of FOXA1 in the biological sample obtained from the test subject is not more than the cutoff value and the expression level of BACH1 has exceeded the cutoff value, pancreatic cancer can be evaluated as having high metastasis ability or invasion ability.

<Method of Predicting Prognosis of Pancreatic Cancer>

The present invention provides a (data acquisition) method of evaluating prognosis of pancreatic cancer in vitro, the method comprising a step of measuring an expression level of BACH1.

In the present invention, prognosis usually means the future outlook for a disease. In predicting prognosis, for example, in a case in which pancreatic cancer has ameliorated or improved or is in the long-term survival or long-term progression-free period, prognosis is favorable, while, for example, pancreatic cancer has recurred, relapsed, or metastasized or is in the short-term survival or long-term progression-free period, prognosis is poor.

Specifically, for example, the cutoff value of the BACH1 expression level is calculated from the receiver operating characteristic (ROC) curve created using clinical data of pancreatic cancer clinical specimens obtained from the database of the Cancer Genome Atlas (TCGA). In a case in which the expression level of BACH1 in the biological sample obtained from the test subject has exceeded the cutoff value, the prognosis can be predicted to be poor, while in a case in which it is not more than the cutoff value, the prognosis can be predicted to be favorable.

Further, in combination with the expression level of FOXA1, which is an epithelial cell marker, the prognosis can be evaluated more accurately. As with BACH1, the cutoff value of the FOXA1 expression level is calculated from the receiver operating characteristic (ROC) curve created using clinical data of pancreatic cancer clinical specimens obtained from the database of TCGA. In a case in which the expression level of FOXA1 in the biological sample obtained from the test subject has exceeded the cutoff value and the expression level of BACH1 is not more than the cutoff value, the prognosis can be predicted to be favorable. Meanwhile, in a case in which the expression level of FOXA1 in the biological sample obtained from the test subject is not more than the cutoff value and the expression level of BACH1 has exceeded the cutoff value, the prognosis can be predicted to be poor.

The therapeutic strategy can be determined based on the results of prognosis prediction as described above. For example, it is possible to determine whether to perform surgical treatment, radiotherapy, chemotherapy, or endocrine therapy (hormone therapy), and which other endocrine agent should be used as endocrine therapy.

<Method of Screening for Pancreatic Cancer Metastasis Suppressant>

The present invention provides a method of screening for a pancreatic cancer metastasis suppressant, comprising: a step of adding a drug candidate substance to cells expressing a BACH1 gene or a reporter gene linked to a promoter of the BACH1 gene: a step of measuring an expression level of the BACH1 gene or reporter gene: and a step of selecting a substance for reducing the expression level.

For example, in a case in which the expression level of the BACH1 gene or the reporter gene linked to the promoter of the BACH1 gene has decreased by specifically, for example, 20% or more, preferably 50% or more, more preferably 90% or more in the presence of a candidate compound as compared with the control without the addition of the candidate compound, the candidate compound can be selected as a candidate for a therapeutic agent for pancreatic cancer.

Any of a biological sample containing cells expressing the BACH1 gene, a cultured cell line expressing the BACH1 gene, and a cultured cell line forcibly expressing the BACH1 gene may be used for cells expressing the BACH1 gene. It is, however, preferable to use a cultured cell line forcibly expressing the BACH1 gene.

The cultured cell line expressing the BACH1 gene is not particularly limited as long as it is a cell line expressing the BACH1 gene, and examples thereof include a cell line from pancreatic cancer cells.

Examples of the cultured cell line forcibly expressing the BACH1 gene include a cultured cell line in which the BACH1 gene is integrated into a plasmid or viral vector for introducing the gene into mammalian cells and transfected into the cells by a usual method such as lipofection. Transfection may be transient or stable.

For cells expressing the reporter gene linked to the promoter of the BACH1 gene, for example, a cultured cell line forcibly expressing the reporter gene, in which the reporter gene is linked to the promoter of the BACH1 gene, incorporated into a plasmid or viral vector for introducing the gene into mammalian cells, and transfected into cells by a conventional method such as lipofection, which is a known method, can be used. Transfection may be transient or stable.

In the case of using the reporter gene linked to the promoter of the BACH1 gene, a region containing about 1 kbp upstream of the transcription initiation site is preferable, and a region containing about 2 kbp upstream of the same is more preferable as the promoter of the BACH1 gene.

As the reporter gene, the luciferase gene, the GFP gene, the chloramphenicol acetyltransferase gene, or the like can be used, and preferably, the luciferase gene or the GFP gene can be used.

According to the present invention, the candidate compound may be any of high-molecular-weight compounds and low-molecular-weight compounds, and is not particularly limited. However, examples of high-molecular-weight compounds include proteins, antibodies, peptides, non-peptidic compounds, nucleic acids, and RNAs. These compounds may be novel compounds, known compounds, and fermentation products, cell extracts, plant extracts, animal tissue extracts, or the like containing these compounds.

By selecting a compound that lowers the expression level of the BACH1 gene from the candidate compounds, as compared with a case in which no candidate compound is added, a substance that can be a therapeutic drug for pancreatic cancer can be obtained.

The concentration of the candidate compound added is not particularly limited as long as it can be confirmed that the expression level of the BACH1 gene is reduced. Further, the addition method, reaction time, reaction temperature, and the like can be appropriately selected according to the test specimen to be used.

<Pancreatic Cancer Metastasis Suppressant>

The present invention provides a pancreatic cancer metastasis suppressant, containing, as an active ingredient, a drug for reducing BACH1 gene expression.

The drug for reducing BACH1 gene expression may be any of high-molecular-weight compounds and low-molecular-weight compounds, and is not particularly limited. However, examples of high-molecular-weight compounds include proteins, antibodies (anti-BACH1 antibodies), peptides, non-peptidic compounds, nucleic acids, and RNAs. It is preferably RNA, more preferably siRNA.

The base sequence of siRNA is not limited as long as it reduces the expression of the BACH1 gene, and examples thereof include the base sequence set forth in SEQ ID NO: 5 or SEQ ID NO: 6.

EXAMPLES

Hereinafter, the present invention will be described in more detail with reference to the Examples below, but needless to say, the scope of the present invention is not limited to the Examples.

Figure 1:
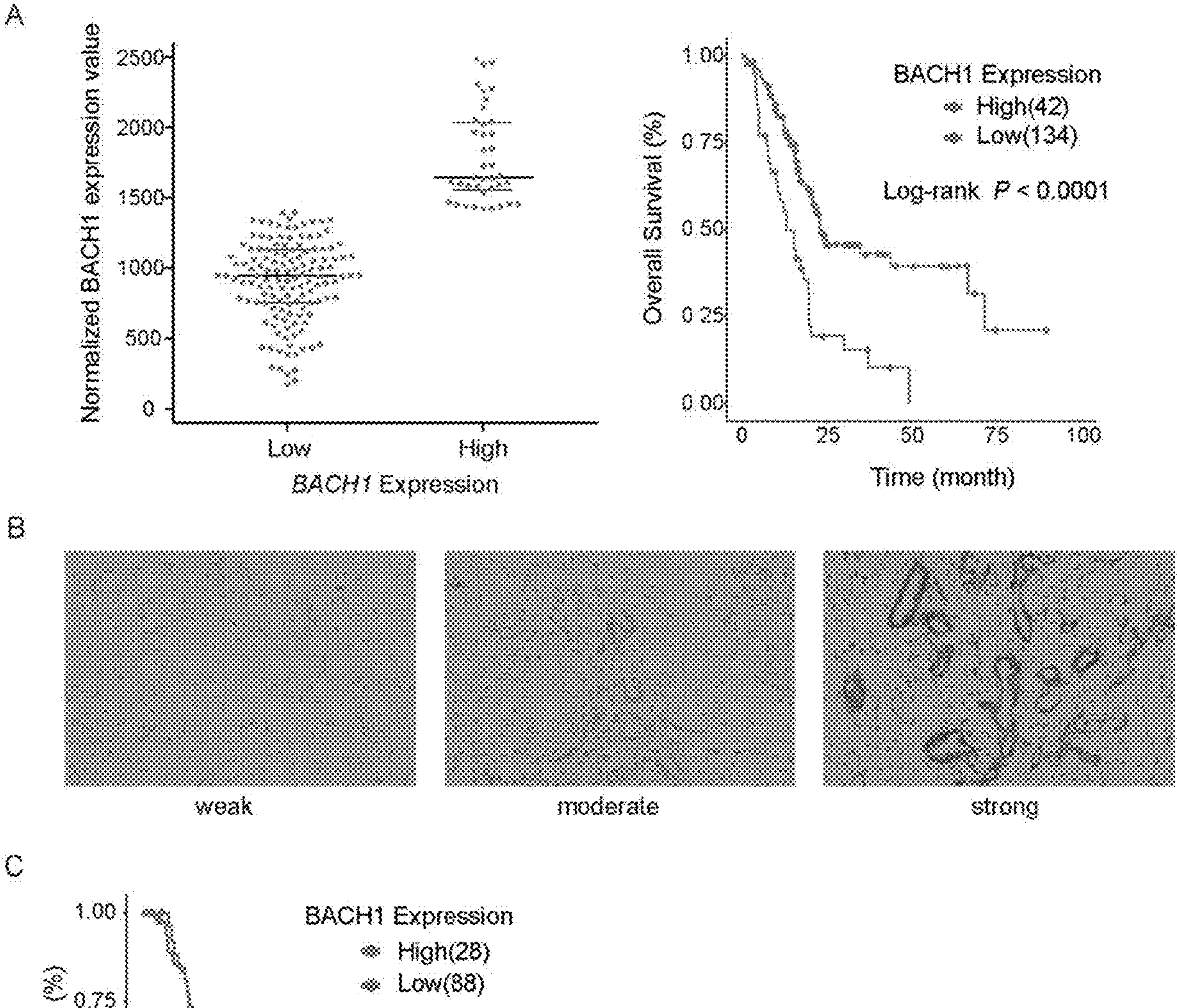
FIG. 1 shows that BACH1 is a predictor of pancreatic cancer prognosis. (A) The RNA sequence data of 176 cases of pancreatic ductal carcinoma with clinical information obtained from the TCGA database were classified into two groups by the cutoff value obtained from the ROC curve based on the expression level of BACH1 (left), and overall survival was analyzed by the Kaplan-Meier method between the two classified groups (right). (B) Immunohistochemistry of 166 clinical specimens of pancreatic cancer was performed using anti-human BACH1 antibody, and the specimens were classified into 3 groups according to the staining ratio (weak: positive rate of less than 10%; moderate: positive rate of from 10% to 50%: strong: positive rate of 50% or more). Typical stained images in this classification are shown (magnification, 200 times). In the subsequent analysis, "weak" and "moderate" were classified as the low BACH1 expression group, and "strong" as the high BACH1 expression group. (C) Overall survival was analyzed by the Kaplan-Meier method in the high BACH1 expression group and the low BACH1 expression group of immunohistochemistry. The P value was determined by the log-rank test.

<Example 1> in Silico Examination of Relationship Between BACH1 Expression Level and Prognosis It was investigated whether there is a relationship between BACH1 expression and prognosis in pancreatic cancer patient specimens registered in the Cancer Genome Atlas (TCGA) database. Based on the cutoff value obtained by software JMP pro v13.1.0 from the receiver operating characteristic (ROC) curve created using clinical data of 176 pancreatic cancer patients available from the database of TCGA, the data were classified into two groups, the low BACH1 expression group (n=134) and the high BACH1 expression group (n=42) (Panel A of FIG. 1, left), and the overall survival (OS) was analyzed by the Kaplan-Meier method.

As a result, it was found that the OS was significantly lower in the high BACH1 expression group (log-rank test; $P<0.0001$, Panel A of FIG. 1, right). This suggests that BACH1 may function as a malignant alteration factor for pancreatic cancer, and in this study, analysis was performed with a focus on the function of BACH1 in pancreatic cancer.

<Example 2> Examination of BACH1 Expression in Clinical Specimens of Pancreatic Cancer In order to investigate the relationship between BACH1 protein expression and prognosis, immunohistochemistry was performed using an anti-human BACH1 monoclonal antibody (9D11, in-house laboratory made antibody, dilution 1:100) using clinical specimens of pancreatic cancer operated at the Department of Hepato-Biliary-Pancreatic Surgery, Tohoku University Hospital. The clinical specimens of pancreatic cancer were from 116 pancreatic cancer cases that underwent resection at the Department of Hepato-Biliary-Pancreatic Surgery, Tohoku University Hospital from 2007 to 2014. The specificity of this anti-human BACH1 monoclonal antibody has been confirmed by experiments using cells subjected to knockdown and knockout (data not shown).

Immunohistochemistry was performed using an anti-human BACH1 monoclonal antibody. A paraffin-embedded section fixed with 10% paraformaldehyde was sliced into 3 μm pieces and adhered and fixed to an antistripping coat slide glass. The sections were deparaffinized with xylene and then dehydrated with ethanol. Antigen activation was performed by boiling with TE (10 mM Tris-HCl pH 8.0, 1 mM EDTA) for 30 minutes. Endogenous peroxidase was inhibited by a reaction with 1% hydrogen peroxidelmethanol for 10 minutes. Blocking was performed with normal goat serum (DakoCytomation, Glostrup, Denmark). The primary antibody reaction was carried out at 4° C. for 24 hours. A secondary antibody reaction was carried out at room temperature for 2 hours using Histofine Simple Stain MAX-PO (M) (Nichirei Biosciences Inc., Tokyo, Japan). Then, color development was carried out with 3,3'-diaminobenzidine dissolved in 0.1M Tris buffer and hydrogen peroxide for 5 minutes, and the nucleus was stained with hematoxylin. In microscopic observation, lymphocytes were used as the internal standard, and evaluated was performed on a three-point scale of weak positive (positive rate of less than 10%), moderate positive (positive rate of 10% to 50%), and strong positive (positive rate of 50% or more) according to the staining intensity. Subsequently, strong positive results were classified as the high BACH1 expression group (n=28), and weak positive results and moderate positive results were classified as the low BACH1 expression group (n=88) (Panel B of FIG. 1).

<Example 3> Relationship Between BACH1 Expression and Overall Survival

To investigate the relationship between BACH1 protein expression and prognosis based on immunohistochemical classification, OS was analyzed by the Kaplan-Meier method.

Consistent with the relationship between BACH1 expression and prognosis using clinical data registered in the TCGA database, OS was significantly lower in the high BACH1 protein expression group (log-rank test; P=0.0213), and thus, it was found that BACH1 is a factor of poor prognosis of pancreatic cancer (Panel C of FIG. 1).

As a result of univariate analysis, it was shown that lymph node metastasis (P=0.0094), distant metastasis (P=0.0004), and BACH1 expression level (P=0.0231) were significant as prognosis factors in OS. Therefore, tissue grade (P=0.0638) was added to these prognosis factor candidates, and multivariate analysis was performed based on the Cox proportional hazard model. In OS, lymph node metastasis (P=0.011) and the BACH1 expression level (P=0.02%) showed significance as independent prognosis factors (Table 1).

TABLE 1

| | Variate analysis | | | |
|---|---|---|---|---|
| | univariate analysis | | multivariate analysis | |
| Variables | HR (95% CI) | P | HR (95% CI) | P |
| Age | 1.009 (0.624-1.690) | 0.971 | | |
| Gender | 1.234 (0.783-1.979) | 0.372 | | |
| hist grade | 2.011 (0.886-3.962) | 0.0638 | 2.279 (0.993-4.573) | 0.0517 |
| Tumor size | 1.346 (0.858-2.133) | 0.1968 | | |
| LN metastasis | 2.131 (1.238-3.910) | 0.0094 | 2.072 (1.175-3.870) | 0.0110 |
| Metastasis | 2.716 (1.512-4.647) | 0.0004 | 1.565 (0.839-2.759) | 0.1528 |
| BACH1 | 1.772 (1.062-2.866) | 0.0231 | 1.781 (1.061-2.900) | 0.0296 |

<Example 4> Relationship Between BACH1 Expression and Cell Proliferation

In order to investigate the influence of BACH1 expression on cancer cell proliferation, knockdown of BACH1 was performed by the RNA interference method using siRNA in pancreatic cancer cell lines AsPC1 and SW1990. Knockdown with siRNA was performed by the following method. siRNA of BACH1 (Stealth RNAi (trademark)siRNA Duplex Oligoribonucleotides, Invitrogen, CA, USA) was used Stealth RNAi (trademark)siRNA Negative Control, Low GC (Thermo Fisher Scientific Inc., MA, USA) was used as a control. SiRNA was introduced by the lipofection method according to the product instructions using Lipofectamine RNAiMAX (Thermo Fisher Scientific Inc.). The siRNA sequences used are as follows.

```
siBACH1-1;
                                    (SEQ ID NO: 5)
5'-GGUCAAAGGACUUUCACAACAUUAA-3'

siBACH1-2;
                                    (SEQ ID NO: 6)
5'-GGGCACCAGGGAAGAUAGUAGUGUU-3'
```

Figure 2:
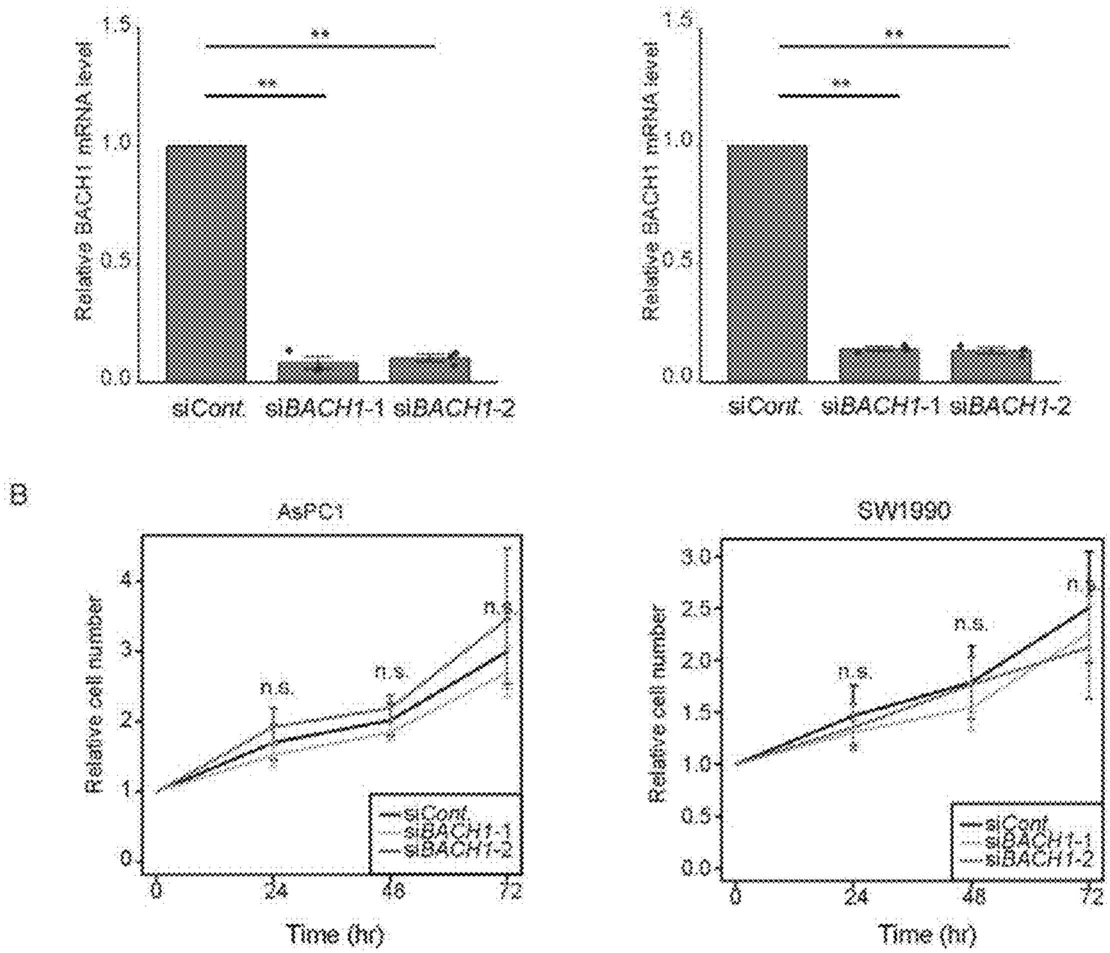
FIG. 2 shows that BACH1 does not affect pancreatic cancer cell proliferation in vitro. (A) Expression levels of BACH1 detected by the RT-qPCR method in BACH1 knockdown (siBACH1) pancreatic cancer cell lines (AsPC1 and SW1990) and their control cells (siCont.) are shown. Each experiment was performed three times or more independently. In the column diagram, the values for each experiment are shown as dots, the average value is shown as a column, and the standard error is shown as a bar. The statistically significant difference was tested by the Student's t-test. The P value is shown (**: $P<0.01$). (B) The change in cell proliferation is shown as a polygonal line graph by measuring the number of cells of BACH1 knockdown (siBACH1) AsPC1 and SW1990 cells and their control cells (siCont.) every 24 hours for up to 72 hours. Each experiment was performed four times independently. The average value is shown as a polygonal line, and the standard error is shown as a bar at each measurement point. The statistically significant difference was tested by the Student's t-test (n.s.: not significant).

As a result, no influence of BACH1 knockdown on cell proliferation was observed in both AsPC1 and SW1990 cell types (FIG. 2).

Figure 3:
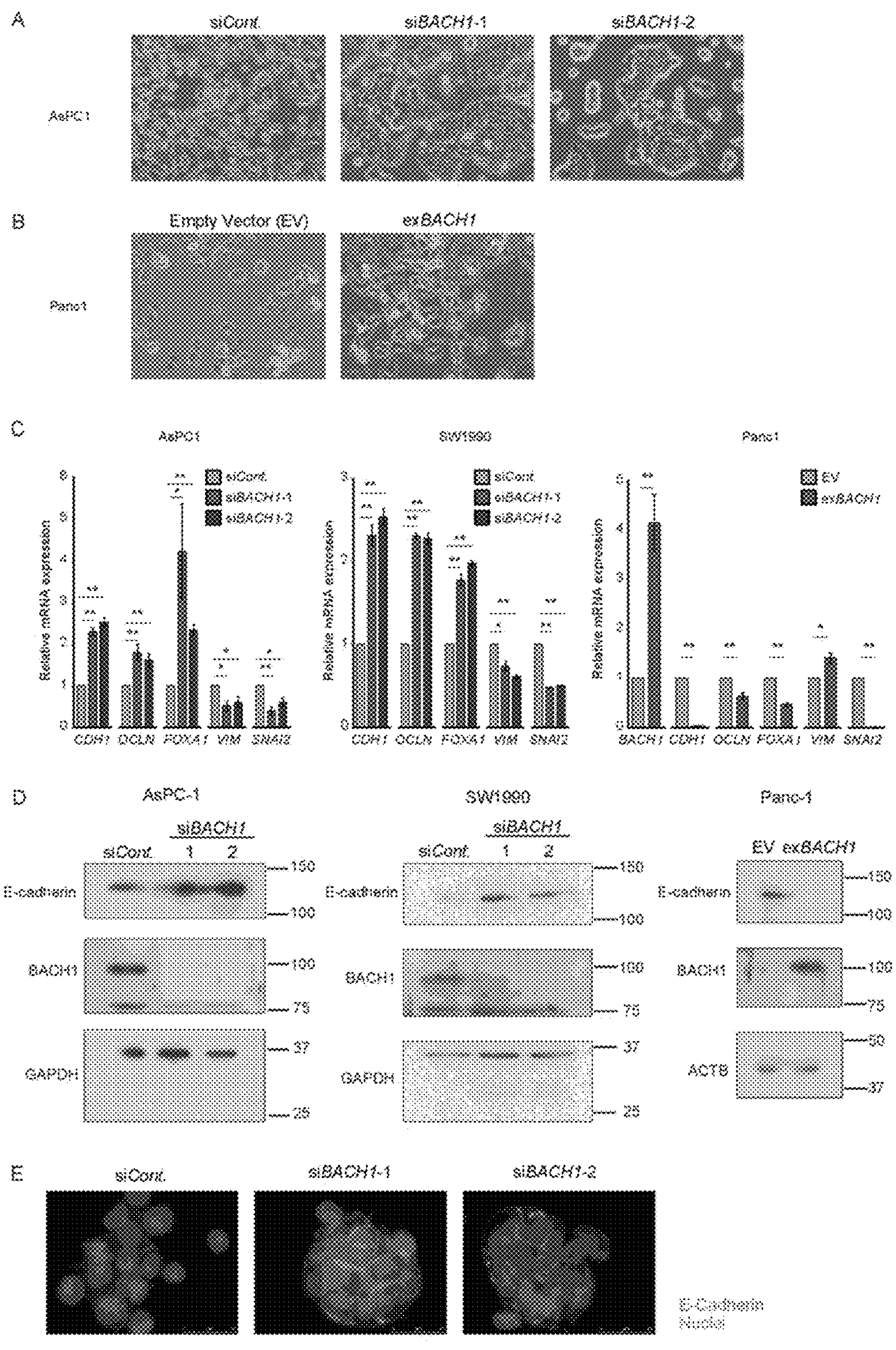
FIG. 3 shows that BACH1 promotes mesenchymal traits of pancreatic cancer cells. Microscopic images of cell morphology are shown: (A) BACH1 knockdown (siBACH1) AsPC1; and (B) BACH1-overexpressing pancreatic cancer cell line (Panc1). The scale represents 100 μm. (C) Expression of epithelial genes (CDH1 (Cadherin 1), OCLN (Occludin), and FOXA1 (Forkhead Box A1)) and mesenchymal genes (VIM (Vimentin) and SNAI2 (Snail Family Transcriptional Repressor 2)) in BACH1 knockdown (siBACH1) AsPC1 and SW1990 cells as well as BACH1-overexpressing (exBA(CHJ) Panc1 cells, and their control cells (siCont. or EV) is shown. Each gene was detected by RT-qPCR. The mRNA expression level of each factor was corrected by the mRNA expression level of β-actin (ACTB). Each experiment was performed three times independently. The average value for each experiment is shown as a column and the standard error is shown as a bar. The statistically significant difference was tested by the Student's t-test. The P value is shown (*: $P<0.05$. **: $P<0.01$). (D) Western blot images (photographs) of E-cadherin, BACH1, and GAPDH or ACTB as an internal standard protein in BACH1 knockdown (siBACH1) AsPC1 and SW1990 cells as well as BACH1-overexpressing (exBACH1) Panc1 cells, and their control cells (siCont. or EV) are shown. (E) Immunofluorescent staining images of E-cadherin in BACH1 knockdown are shown. The scale represents 25 μm.

<Example 5> Changes in Cell Morphology by BACH1 Knockdown and Overexpression The pancreatic cancer cell line AsPC1 in which BACH1 was knocked down by the same procedures as in Example 4 showed strong cell-cell adhesion and epithelial-like cell morphology as shown in Panel A of FIG. 3 (Panel A of FIG. 3).

Therefore, BACH1 was overexpressed in Panc1, which has a lower expression level of BACH1 protein than AsPC1. For overexpression, plasmid was introduced into Panc1 cultured in a 6-cm culture dish using a commercially available transfection kit, Fugene (registered trademark) HD, according to the attached product instructions. As a control, 7.2 μg of a commercially available vector pcDNA3.1 (−) (Addgene) was introduced. Meanwhile, for overexpression, 7.2 μg of pCMV2-BACH1, which is a vector prepared by incorporating the BACH1 gene that is the nucleotide sequence shown in SEQ ID NO: 1 into a commercially available vector, pCMV2, was introduced, and 1 μg of pcDNA3.1 (−) was introduced for drug selection. Culture was carried out for 2 weeks in Panc1 medium supplemented with 2,000 μg/mL G418 (Calbiochem. Germany). Culture was carried out in a medium prepared by adding 20% fetal bovine serum (FBS, Sigma Aldrich), 0.1 mg/mL penicillin/streptomycin (GIBCO. NY, USA), 10 mM HEPES (GIBCO), and SW1990 to RPMI 1640 medium (Sigma Aldrich, MO, USA) for AsPC1 and in a medium prepared by adding 10% FBS, 0. 1 mg/mL penicillin/streptomycin, and 10 mM HEPES to RPMI 1640 medium for Panc1. After the culture, colonies formed by cells that survived by acquiring drug resistance were isolated under a microscope and cloned.

As a result, BACH1-overexpressing Panc1 showed weaker cell-cell adhesion, contrary to that of BACH1 knockdown AsPC1, and showed pseudopodia-like distorted cell morphology (Panel B of FIG. 3). In other words, BACH1 was considered to promote epithelial-to-mesenchymal transition (EMT).

Therefore, the expression of epithelial genes (CDH1, OCLN, FOXA1) and the mesenchymal genes (VIM and SNAI2) was confirmed by quantitative RT-PCR according to the procedures described below. First, RNA extraction was performed using the RNeasy (registered trademark) Plus Mini Kit (Qiagen, Germany) according to the attached product instructions. For cDNA synthesis, the extracted RNA was reverse-transcribed using Omniscript Reverse Transcription kits (Qiagen) according to the attached product instructions. For the reverse transcription reaction, 1 μg of RNA and 200 ng of Random primer (Invitrogen) were used, the reaction was carried out at 37° C. for 60 minutes, and the reverse transcription reaction was terminated by heat treatment at 93° C. for 5 minutes. A quantitative PCR method using SYBR (registered trademark) Green I as an intercalator was used for measuring the expression level of the gene of interest. According to the attached product instructions, each gene-specific primer from cDNA was used and measured with a quantitative PCR machine LightCycler (registered trademark) Nano (Roche) using LightCycler (registered trademark) Fast Start DNA Master SYBR GreenI (Roche, Swiss). The mRNA expression level of the gene of interest was corrected by the expression level of the internal standard gene and evaluated by relative quantification for comparison between specimens. The β-actin gene (ACTB) was used as the internal standard gene. The sequence of each primer is as follows.

```
ACTB
                              (SEQ ID NO: 7)
(Forward) 5'-ATTTGCGGTGGACGATGGAG-3'

                              (SEQ ID NO: 8)
(Reverse) 5'-AGAGATGGCCACGGCTGCTT-3

BACH1
                              (SEQ ID NO: 9)
(Forward) 5'-AATCGTAGGCCAGGCTGATG-3'

                             (SEQ ID NO: 10)
(Reverse) 5'-AGCAGTGTAGGCAAACTGAA-3'

CDHI
                              (SEQ D NO: 11)
(Forward) 5'-TCCTGGCCTCAGAAGACAGA-3'

                             (SEQ ID NO: 12)
(Reverse) 5'-CCTTGGCCAGTGATGCTGTA-3'

OCLN
                             (SEQ ID NO: 13)
(Forward) 5'-GAGTTGACAGTCCCATGGCA-3'

                             (SEQ ID NO: 14)
(Reverse) 5'-CTGAAGTCATCCACAGGCGA-3'

FOXA1
                             (SEQ ID NO: 15)
(Forward) 5'-GGTGGCTCCAGGATGTTAGG-3'

                             (SEQ ID NO: 16)
(Reverse) 5'-CCCAGGCCTGAGTTCATGTT-3'

VIM
                             (SEQ ID NO: 17)
(Forward) 5'-GGACCAGCTAACCAACGACA-3'

                             (SEQ ID NO: 18)
(Reverse) 5'-GGGTGTTTTCGGCTTCCTCT-3

SNAI2
                             (SEQ ID NO: 19)
(Forward) 5'-CAACGCCTCCAAAAAGCCAA-3'
```

-continued

```
                             (SEQ ID NO: 20)
(Reverse) 5'-ACAGTGATGGGGCTGTATGC-3'
```

As a result, in the BACH1 knockdown cells (AsPC1, SW11990), the expression of the epithelial genes increased, compared to control cells, while the expression of the mesenchymal genes was significantly decreased. In addition, in the BACH1-overexpressing cells (Panc1), the expression of the epithelial genes decreased, and the expression of the mesenchymal genes VIM increased, but the expression of SNA12 was decreased (Panel C of FIG. 3).

Figure 4:
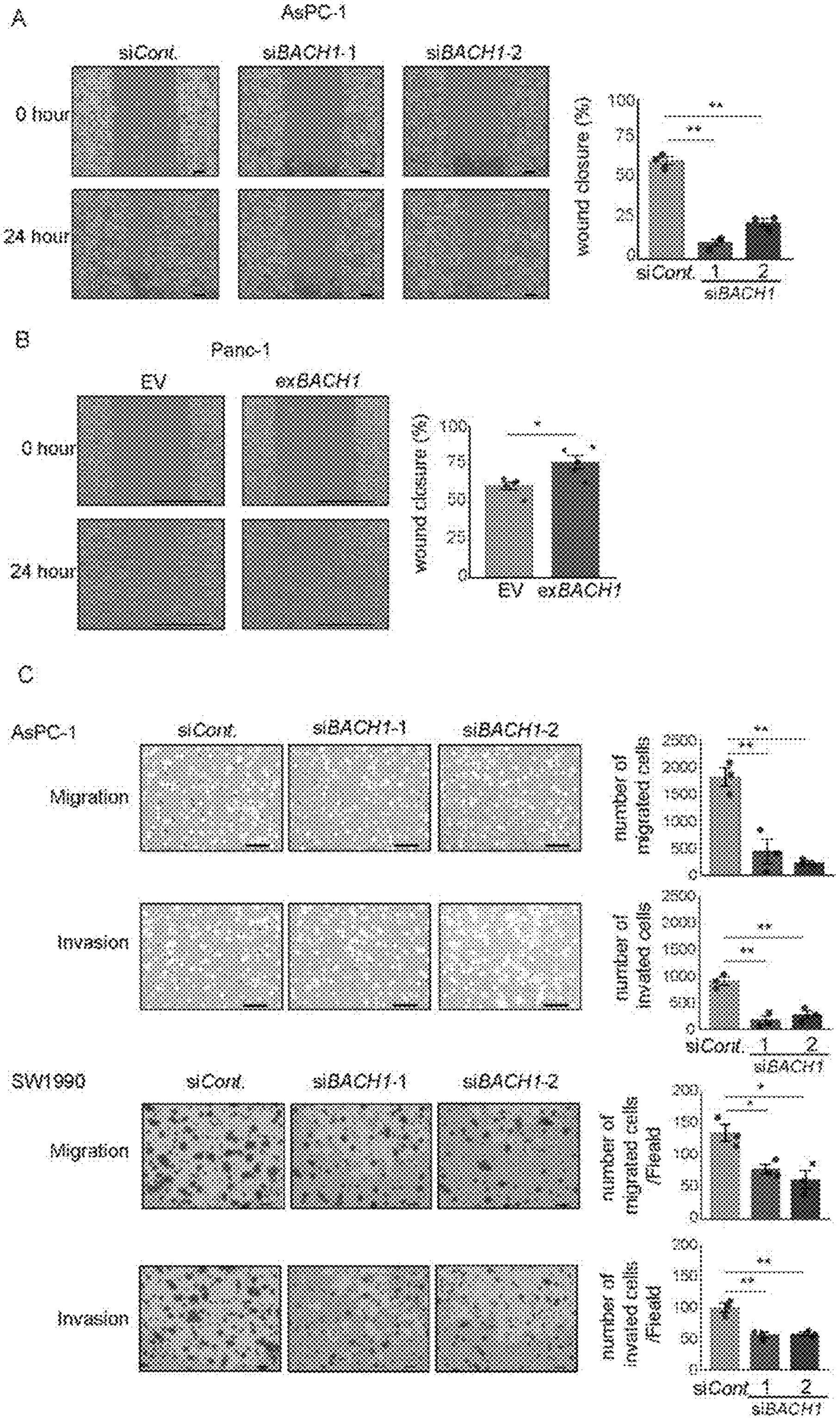
FIG. 4 shows that BACH1 enhances migration ability and invasion ability of pancreatic cancer cell lines in vitro.

Further, in AsPC1, the E-cadherin protein was detected by Western blotting. After preparing the protein by suspending cells in SDS sample buffer (0.0625M Tris-HCl (pH 6.8), 2.2% SDS, 10% glycerol, 0.01% BPB, 5% β-ME) and solubilizing them, the cells were denatured at 95° C. for 5 minutes. The total protein extract of the heat-denatured cells was electrophoresed on a 7.5% to 12% polyacrylamide gel and developed according to the molecular weight. By the wet method, the protein was transferred from the gel to a polyvinylidene fluoride membrane (PVDF membrane. Millipore. Germany). The PVDF membrane after transfer was shaken at room temperature for 1 hour in T-TBS (TBS containing 0.05% Tween 20 (25 mM Tris-HCl (pH 7.4), 137 mM NaCl, 3 mM KCl)) to which skim milk (Wako Jyun-Yaku Co., Osaka, Japan) having a final concentration of 3% was added for blocking treatment. For the primary antibody, the anti-BACH1 antibody (1:1000, in-house laboratory made), the anti-GAPDH antibody (1:5000, ab8245, Abcam, England), the anti-β-Actin antibody (1:1000, GTX109639, GeneTeX, CA, USA), and the anti-E-cadherin antibody (1:1000, ab1416, Abcam) were diluted with the above-described blocking solution and reacted at 4° C. overnight. HRP conjugated anti-mouse IgG blotting reagents (1:5000, GE Healthcare, NJ, USA) diluted with the above blocking solution were prepared, added to the PVDF membrane after the primary antibody reaction, and reacted at room temperature for 60 minutes. After washing with wash buffer, detection was performed by sensitizing to X-film (GE Healthcare) by chemiluminescence using SuperSignal West Pico (Thermo Fisher Scientific Inc.) or ECL Plus Western Blotting Substrate (Thermo Fisher Scientific Inc.). As a result, following gene expression (CDH1, Panel C of FIG. 3). BACH1 knockdown increased protein expression level (Panel D of FIG. 4, left). The same effects were confirmed not only in AsPC1 but also in SW1990 (Panel D of FIG. 3, center). Further, it was found that E-cadherin gene expression and protein expression decreased in BACH1-overexpressing Panc1 (Panel D of FIG. 3, right). Considering that E-cadherin is a typical marker protein of epithelial cells and functions as an intercellular adhesion factor (Panel E of FIG. 3), it was suggested that this is one of the factors that changed the cell morphology. These results suggest that BACH1 is important for the expression and maintenance of mesenchymal cell traits in pancreatic cancer.

<Example 6> Influence of BACH1 on Migration Ability and Invasion Ability

In order to investigate whether BACH1 can promote the migration ability and invasion ability of pancreatic cancer cells, scratch assay was performed according to the following procedures so as to confirm the migration ability. First, a wound (straight line) was formed on the confluent cells on a 6-well plate using a 1,000 μL pipette tip, and the cell moving area was measured by comparing the wound area immediately after the wound formation and that 24 hours after the wound formation. In addition, the moving area was measured by using the software Image J (NIH, https://imagej.nih.gov/ij.) to measure the number of pixels, and similar experiments were performed independently three or more times. As a result, the migration ability significantly decreased in BACH1 knockdown AsPC1, compared to the control cells (Panel A of FIG. 4), while the migration ability significantly increased in BACH1-overexpressing Panc1, compared to the control cells (Panel B of FIG. 4).

Further, the migration ability and invasion ability were confirmed using the Boyden-chamber method. First, a medium containing serum (20% FBS for AsPC1 and 10% FBS for SW1990) was added to a lower 24-well plate, and an insert was allowed to stand on it, and then cells suspended in serum-free medium ($2\times10^5$ cells for AsPC1 and $1\times10^5$ cells for SW1990) were seeded in this insert. After 24 hours, all cells present on the upper surface of the insert membrane were removed with a cotton swab. Then, the cells that had moved to the lower surface of the insert membrane were fixed and stained by immersing them in a crystal violet solution (4.2% formalin, 0.05% crystal violet, 10% ethanol) for 10 minutes. The stained membrane was thoroughly washed with distilled water, dried, and the numbers of migrating and invading cells were visually counted under a microscope. A single experiment was repeated twice for each sample, and the number of cells in the entire membrane was counted for AsPC1. The number of cells was counted in each of the 5 independent fields and averaged for SW1990. The same experiment was performed independently three or more times. As a result, the migration ability and invasion ability significantly decreased in BACH1 knockdown AsPC1 and SW1990 (Panel C of FIG. 4).

From the above, it was found that BACH1 promotes the migration ability and invasion ability in pancreatic cancer cells.

<Example 7> Establishment of BACH1 Knockout Cell Lines

In order to verify in vivo whether BACH1 functions to promote metastasis in experiments of implantation in mice, BACH1 knockout pancreatic cancer cell lines were prepared using the CRISPR/CAS9 system. The CRISPR/CAS9 system was used according to the following method. Each of the following guide RNAs were ligated to a viral vector lentiCRISPR v2 (Addgene, MA, USA) treated with restriction enzyme BsmB1 (recognition sequence: 5'CGTCTC3'), thereby preparing viral vectors each having guide RNA of interest. 293T cells, which are human fetal-derived renal epithelial cells, were transfected with Fugene (registered trademark) HD (Promega, WI, USA) according to the product instructions, and 2 days later, the culture supernatant was collected as a virus solution. AsPC1 was infected with a virus having the guide RNA of interest using the collected virus solution, 10 μg/mL puromycin (Sigma Aldrich) was added to the medium, and drug selection was performed for 3 weeks, following which a single clone was obtained by isolating the formed colonies under a microscope. Gene mutation and the loss of protein expression were confirmed by genomic sequencing and Western blotting, respectively. The single guide RNA (sgRNA) targeted the following sequences of BACH1.

```
                                        (SEQ ID NO: 21)
Guide RNA-1; 5'-CCGCGCUCACCGGUCCGUGCUGG-3'

                                        (SEQ ID NO: 22)
Guide RNA-2; 5'-CCACUCAAGAAUCGUAGGCCAGG-3'
```

It was confirmed that the prepared BACH1 knockout cells contained a 13-base deletion mutation (sgBACH1-1) or a 1-base insertion mutation (sgBACH1-2) of interest in the target regions of the two types of guide RNA shown in the reference sequence of Panel A of FIG. 5 (Panel A of FIG. 5). In addition, the loss of BACH1 protein expression was confirmed by Western blotting (Panel B of FIG. 5). Further, it was confirmed by quantitative RT-PCR whether BACH1 knockout increases the expression of the epithelial genes and decreases the expression of the mesenchymal genes as in the case of BACH1 knockdown. As a result, significant upregulation of epithelial genes was observed, but no decrease in mesenchymal genes was observed (Panel C of FIG. 5). In addition, when the E-cadherin protein expression level was confirmed by Western blotting, CDH1 expression was increased in both sgBACH1-1 and sgBACH1-2 cells (Panel C of FIG. 5) while the E-cadherin protein expression level significantly increased only in sgBACH1-2 cells, similar to the results of siRNA interference (Panel B of FIG. 5). Further, immunofluorescent staining was performed, thereby confirming changes in the expression levels of the BACH1 protein and the E-cadherin protein. Immunofluorescent staining was performed by the following method. Cells cultured on a glass slide were fixed in 4% formaldehyde/PBS for 10 minutes. The cells on the slide glass were immersed in an antibody solution obtained by diluting a primary antibody BACH1 (9D11, in-house laboratory made) and E-cadherin (ab1416, abcam) 200-fold with 1% bovine serum albumin (BSA)/PBS, and reacted at 37° C. for 1 hour. After being washed with PBS, the cells were immersed in an antibody solution obtained by diluting a secondary antibody (anti-mouse IgG antibody-FITC (F3008, Sigma Aldrich)) 1000-fold with 1% BSA/PBS, and reacted at 37° C. for 1 hour. After the cells were washed with PBS, nuclear staining was performed with 20 μg/mL Hoechst 33342/PBS, and the cells encapsulated with VECTASHIELD Mounting Medium (Funakoshi, Tokyo, Japan) were examined using a high-speed fluorescence imaging system AF6500 (Leica, Germany), which is a fluorescence inverted microscope. As a result, the loss of BACH1 protein and the increased E-cadherin protein expression level in the cells were confirmed (Panels D and E of FIG. 5).

<Example 8> Influence of BACH1 on Tumorigenesis and Metastasis Ability

To analyze the function of BACH1 in individual mice, orthotopic cancer cell implantation of BACH1 knockout AsPC1 cells and their control cells into the pancreatic tissue of hyperimmune-deficient mice (NOG (NOD.Cg-$Prkdc^{scid}Il2rg^{tm1Sug}$/ShiJic) mice) was performed. Six- to eight-week-old NOG mice were used in experiments. After intraperitoneal administration of a mixture of three different anesthetics (medetomidine: 0.3 mg/kg: midazolam: 4 mg/kg; butorphanol: 5 mg/kg) to mice, orthotopic implantation to the pancreas was performed using BACH1 wild-type AsPC1 and BACH1 knockout AsPC1. In orthotopic implantation, the upper left abdomen was opened 1.5 cm, the pancreas was released from the body, $10^4$ cells (suspended in 100 μL of PBS) were transplanted under the capsule of the tail of the pancreas using a 27 G needle. After the implantation, the pancreas was returned to the body and the abdomen was closed with a 3-0 absorbent thread. After 5 weeks, the weight of pancreatic tissue, the number of metastases to the liver and the number of metastases to the mesentery, diaphragm, and peritoneum as peritonea dissemination were visually measured by dissection. Panel A of FIG. 6 shows typical images of the pancreas, liver, and mesentery at the time of dissection. Consistent with the results of cell proliferation in vitro, there was no significant difference in tumor proliferation ability in the pancreas (xenograft) (Panel B of FIG. 6, left). However, liver metastasis and peritoneal dissemination were significantly reduced in BACH1 knockout AsPC1 (Panel B of FIG. 6, center and right). The results showed that BACH1 does not affect primary tumorigenesis in pancreatic cancer cells, but enhances metastasis ability.

<Example 9> Examination of Prognosis Prediction with Combination of BACH1 and FOXA1

The relationship between FOXA1 expression and prognosis was analyzed using RNA-sequence data of pancreatic cancer patients from TCGA. The higher the expression of FOXA1, the better the prognosis (Panel A of FIG. 7). In addition, the function of BACH1 in prognosis was re-evaluated by further combining and analyzing the factors downstream of BACH1 and the expression of BACH1. Accordingly, the results showed that the prognosis was the worst with the combination of high expression of BACH1 and low expression of FOXA1 in which BACH1 strongly exerts its transcriptional repressive function while the prognosis was favorable with the combination of low expression of BACH1 and high expression of FOXA1 in which BACH1 has lost its transcriptional repressive function (Panel B of FIG. 7). The result show that BACH1 can be used as a biomarker for excellent prognosis prediction of pancreatic cancer by considering the functional evaluation using the expression of its downstream gene, the FOXA1 gene. BACH1 is also considered to be an indicator of the strength of the metastatic tendency of pancreatic cancer.

The invention claimed is:

1. A method of predicting prognosis and treating pancreatic cancer in a subject, the method comprising:

a step of measuring an expression level of a BACH1 gene in a biological sample obtained from a human subject, wherein the biological sample is selected from a group consisting of cells or tissues of the pancreas, cells or tissues around the pancreas, blood or lymph that can contain pancreatic cancer cells, and circulating cancer cells in blood;

a step of predicting the subject as having a poor prognosis of pancreatic cancer by measuring the expression level of the BACH1 gene as being above a cutoff value of the BACH1 expression level calculated from a receiver operating characteristic (ROC) curve; and a step of performing surgical treatment, radiotherapy, chemotherapy, or endocrine therapy on the subject by the determination of therapeutic strategy based on the results of the prognosis prediction.

2. A method of predicting prognosis and treating pancreatic cancer in a subject the method comprising;

a step of measuring an expression level of a BACH1 gene and an expression level of FOXA1 in a biological sample obtained from a human subject, wherein the biological sample is selected from a group consisting of cells or tissues of the pancreas, cells or tissues around the pancreas, blood or lymph that can contain pancreatic cancer cells, and circulating cancer cells in blood;

a step of predicting the subject has poor prognosis pancreatic cancer when the subject has an expression level of the BACH1 gene above the cutoff value of the BACH1 expression level calculated from a receiver operating characteristic (ROC) curve and has an expression level of a FOXA1 gene below a cutoff value of the FOXA1 expression level calculated from a receiver operating characteristic (ROC) curve; and a step of performing surgical treatment, radiotherapy, chemotherapy, or endocrine therapy on the subject when the subject is predicted to have poor prognosis pancreatic cancer.

* * * * *

```
                        SEQUENCE LISTING

<160> NUMBER OF SEQ ID NOS: 25

<210> SEQ ID NO 1
<211> LENGTH: 5475
<212> TYPE: DNA
<213> ORGANISM: Homo sapiens
<220> FEATURE:
<221> NAME/KEY: CDS
<222> LOCATION: (119)..(2329)

<400> SEQUENCE: 1

tcgcccccgc cgggcgctct cgcttcagtc agtcgggccg cgccgcgcct cagctctggt      60

tgatgataat tagaagcatg ctttccactg aacttcccga caacatttgt tatgcaga      118

atg tct ctg agt gag aac tcg gtt ttt gcc tat gaa tct tct gtg cat      166
Met Ser Leu Ser Glu Asn Ser Val Phe Ala Tyr Glu Ser Ser Val His
1               5                   10                  15

agc acc aat gtt tta ctc agc ctt aat gac cag cgg aag aaa gat gtg      214
Ser Thr Asn Val Leu Leu Ser Leu Asn Asp Gln Arg Lys Lys Asp Val
            20                  25                  30

ctg tgc gat gtc acc atc ttt gtg gag gga cag cgg ttc cgc gct cac      262
Leu Cys Asp Val Thr Ile Phe Val Glu Gly Gln Arg Phe Arg Ala His
        35                  40                  45

cgg tcc gtg ctg gcg gca tgc agc agt tac ttc cac tca aga atc gta      310
Arg Ser Val Leu Ala Ala Cys Ser Ser Tyr Phe His Ser Arg Ile Val
    50                  55                  60

ggc cag gct gat gga gag ctg aac att act ctt cca gaa gag gtg aca      358
Gly Gln Ala Asp Gly Glu Leu Asn Ile Thr Leu Pro Glu Glu Val Thr
65                  70                  75                  80

gtt aaa gga ttt gaa cct tta att cag ttt gcc tac act gct aaa ctg      406
Val Lys Gly Phe Glu Pro Leu Ile Gln Phe Ala Tyr Thr Ala Lys Leu
                85                  90                  95

att tta agt aaa gag aat gtg gat gaa gtg tgc aaa tgt gtg gag ttt      454
Ile Leu Ser Lys Glu Asn Val Asp Glu Val Cys Lys Cys Val Glu Phe
            100                 105                 110

tta agt gta cat aat att gag gaa tcc tgc ttt cag ttt ctg aaa ttt      502
Leu Ser Val His Asn Ile Glu Glu Ser Cys Phe Gln Phe Leu Lys Phe
        115                 120                 125

aag ttt ttg gac tcc act gca gac cag caa gaa tgc cca aga aaa aaa      550
Lys Phe Leu Asp Ser Thr Ala Asp Gln Gln Glu Cys Pro Arg Lys Lys
    130                 135                 140
```

-continued

```
tgc ttt tca tca cac tgt cag aaa aca gac ctt aaa ctt tca ctt ttg      598
Cys Phe Ser Ser His Cys Gln Lys Thr Asp Leu Lys Leu Ser Leu Leu
145                 150                 155                 160

gac cag agg gat cta gaa act gat gaa gtg gag gaa ttt ctg gaa aat      646
Asp Gln Arg Asp Leu Glu Thr Asp Glu Val Glu Glu Phe Leu Glu Asn
                165                 170                 175

aaa aat gtt cag act cct cag tgt aaa ctc cgc agg tat caa gga aat      694
Lys Asn Val Gln Thr Pro Gln Cys Lys Leu Arg Arg Tyr Gln Gly Asn
            180                 185                 190

gca aaa gcc tca cct cct cta caa gac agt gcc agt cag aca tat gag      742
Ala Lys Ala Ser Pro Pro Leu Gln Asp Ser Ala Ser Gln Thr Tyr Glu
        195                 200                 205

tcc atg tgc tta gag aag gat gct gct ctg gcc ttg cct tct tta tgc      790
Ser Met Cys Leu Glu Lys Asp Ala Ala Leu Ala Leu Pro Ser Leu Cys
    210                 215                 220

ccc aaa tac aga aaa ttc caa aaa gca ttt gga act gac aga gtc cgt      838
Pro Lys Tyr Arg Lys Phe Gln Lys Ala Phe Gly Thr Asp Arg Val Arg
225                 230                 235                 240

act ggg gaa tct agt gtc aaa gac att cat gct tct gtt cag cca aat      886
Thr Gly Glu Ser Ser Val Lys Asp Ile His Ala Ser Val Gln Pro Asn
                245                 250                 255

gaa agg tct gaa aat gaa tgc ctg gga gga gtc ccg gag tgt aga gat      934
Glu Arg Ser Glu Asn Glu Cys Leu Gly Gly Val Pro Glu Cys Arg Asp
            260                 265                 270

ttg cag gtg atg tta aaa tgt gac gaa agt aaa tta gca atg gaa cct      982
Leu Gln Val Met Leu Lys Cys Asp Glu Ser Lys Leu Ala Met Glu Pro
        275                 280                 285

gaa gaa acg aag aaa gat cct gct tct cag tgc cca act gaa aaa tca     1030
Glu Glu Thr Lys Lys Asp Pro Ala Ser Gln Cys Pro Thr Glu Lys Ser
    290                 295                 300

gaa gtg act cct ttc ccc cac aat tct tcc ata gac cct cat gga ctt     1078
Glu Val Thr Pro Phe Pro His Asn Ser Ser Ile Asp Pro His Gly Leu
305                 310                 315                 320

tat tct ttg tct ctt tta cac aca tat gac caa tat ggt gac ttg aat     1126
Tyr Ser Leu Ser Leu Leu His Thr Tyr Asp Gln Tyr Gly Asp Leu Asn
                325                 330                 335

ttt gct ggt atg caa aac aca aca gtg tta aca gaa aag cct ttg tca     1174
Phe Ala Gly Met Gln Asn Thr Thr Val Leu Thr Glu Lys Pro Leu Ser
            340                 345                 350

ggt aca gac gtc caa gaa aaa aca ttt ggt gaa agt cag gat tta cct     1222
Gly Thr Asp Val Gln Glu Lys Thr Phe Gly Glu Ser Gln Asp Leu Pro
        355                 360                 365

ttg aaa tcc gac ttg ggc acc agg gaa gat agt agt gtt gca tct agt     1270
Leu Lys Ser Asp Leu Gly Thr Arg Glu Asp Ser Ser Val Ala Ser Ser
    370                 375                 380

gat agg agt agt gtg gag cga gaa gtg gca gaa cac cta gca aaa ggc     1318
Asp Arg Ser Ser Val Glu Arg Glu Val Ala Glu His Leu Ala Lys Gly
385                 390                 395                 400

ttc tgg agt gac att tgc agc acg gac act cct tgc caa atg cag tta     1366
Phe Trp Ser Asp Ile Cys Ser Thr Asp Thr Pro Cys Gln Met Gln Leu
                405                 410                 415

tca cct gct gtg gcc aaa gat ggc tca gaa cag atc tca cag aaa cgg     1414
Ser Pro Ala Val Ala Lys Asp Gly Ser Glu Gln Ile Ser Gln Lys Arg
            420                 425                 430

tct gag tgt ccg tgg tta ggt atc agg att agt gag agc cca gaa cca     1462
Ser Glu Cys Pro Trp Leu Gly Ile Arg Ile Ser Glu Ser Pro Glu Pro
        435                 440                 445

ggt caa agg act ttc aca aca tta agt tct gtc aac tgc cct ttt ata     1510
Gly Gln Arg Thr Phe Thr Thr Leu Ser Ser Val Asn Cys Pro Phe Ile
    450                 455                 460
```

-continued

```
agt act ctg agt act gaa ggc tgt tca agc aat ttg gaa att gga aac     1558
Ser Thr Leu Ser Thr Glu Gly Cys Ser Ser Asn Leu Glu Ile Gly Asn
465                 470                 475                 480

gat gat tat gtt tca gaa ccc cag caa gaa cct tgc cca tat gct tgt     1606
Asp Asp Tyr Val Ser Glu Pro Gln Gln Glu Pro Cys Pro Tyr Ala Cys
                485                 490                 495

gtc att agc ttg gga gac gac tct gag acg gac acc gaa gga gac agt     1654
Val Ile Ser Leu Gly Asp Asp Ser Glu Thr Asp Thr Glu Gly Asp Ser
            500                 505                 510

gaa tcc tgt tca gcc aga gaa caa gaa tgt gag gta aaa ctg cca ttc     1702
Glu Ser Cys Ser Ala Arg Glu Gln Glu Cys Glu Val Lys Leu Pro Phe
        515                 520                 525

aat gca caa cgg ata att tca ctg tct cga aat gat ttt cag tcc ttg     1750
Asn Ala Gln Arg Ile Ile Ser Leu Ser Arg Asn Asp Phe Gln Ser Leu
    530                 535                 540

ttg aaa atg cac aag ctt act cca gaa cag ctg gat tgt atc cat gat     1798
Leu Lys Met His Lys Leu Thr Pro Glu Gln Leu Asp Cys Ile His Asp
545                 550                 555                 560

att cga aga aga agt aaa aac aga att gct gca cag cgc tgt cgc aag     1846
Ile Arg Arg Arg Ser Lys Asn Arg Ile Ala Ala Gln Arg Cys Arg Lys
                565                 570                 575

aga aaa ctt gac tgt ata cag aat ctt gaa tca gaa att gag aag ctg     1894
Arg Lys Leu Asp Cys Ile Gln Asn Leu Glu Ser Glu Ile Glu Lys Leu
            580                 585                 590

caa agt gaa aag gag agc ttg ttg aag gaa aga gat cac att ttg tca     1942
Gln Ser Glu Lys Glu Ser Leu Leu Lys Glu Arg Asp His Ile Leu Ser
        595                 600                 605

act ctg ggc gag aca aag cag aac cta act gga ctt tgc cag aaa gtt     1990
Thr Leu Gly Glu Thr Lys Gln Asn Leu Thr Gly Leu Cys Gln Lys Val
    610                 615                 620

tgt aaa gaa gca gct ctg agt caa gaa caa ata cag ata ctc gcc aag     2038
Cys Lys Glu Ala Ala Leu Ser Gln Glu Gln Ile Gln Ile Leu Ala Lys
625                 630                 635                 640

tac tca gct gca gat tgc cca ctt tca ttt tta att tct gaa aaa gat     2086
Tyr Ser Ala Ala Asp Cys Pro Leu Ser Phe Leu Ile Ser Glu Lys Asp
                645                 650                 655

aaa agt act cct gat ggt gaa ctg gcg tta cca tca att ttc agt tta     2134
Lys Ser Thr Pro Asp Gly Glu Leu Ala Leu Pro Ser Ile Phe Ser Leu
            660                 665                 670

tct gac cgg cct cca gca gtg ctg cct ccc tgt gcc aga gga aac agt     2182
Ser Asp Arg Pro Pro Ala Val Leu Pro Pro Cys Ala Arg Gly Asn Ser
        675                 680                 685

gag cct ggc tac gcg cga ggg cag gag tcc cag cag atg tcc aca gcc     2230
Glu Pro Gly Tyr Ala Arg Gly Gln Glu Ser Gln Gln Met Ser Thr Ala
    690                 695                 700

acc tct gag caa gct ggg cct gcg gaa cag tgt cgt cag agt ggt ggg     2278
Thr Ser Glu Gln Ala Gly Pro Ala Glu Gln Cys Arg Gln Ser Gly Gly
705                 710                 715                 720

atc tca gat ttc tgt cag cag atg act gat aaa tgt act act gat gag     2326
Ile Ser Asp Phe Cys Gln Gln Met Thr Asp Lys Cys Thr Thr Asp Glu
                725                 730                 735

taa acttgcattc acttccttca aaccatctaa ttttctcctg aagttttggc          2379

agcgtcttga aagcctaata tgaccatctg ttgctcaaca atactgtttt tttcctttag   2439

tagtttacca caagggaatt tcctttaagt caaccatgat ttctccttga tttctacaag   2499

agacaaagaa atgattttgc ctcctggata tcagaaaaat ccatgtgaaa atgtagtaaa   2559

cctttaaaac tcatgtttta aagaataata actctagtaa taactcttcc tgctattcag   2619
```

-continued

```
aataagtagg agaatgaaaa ctgcagcata tcagacagca atttaacagc ttgaaacatc   2679
tacagatagt tcctactaaa agaagtggcc tgcagaagtt taataatttg actttttttct  2739
aatattttag tttgaaagaa aatttcttcc caagcaatgc taatagagtt ctattcttag   2799
aagcagggtg tcagctactg ggaatatttt tgtagagctg cattgtgaaa aaaagatggt   2859
cttacctgaa tcttagggct ttgttcttcg gctcctaaaa tcaggcttta agctacattg   2919
ggaagattta gtaaataggc aagtggttgg cctaagacgg gggctgcttc tcctcttcag   2979
tatggactct agaaagtctg gctacatgaa tagatttaag tgtcactttc cctccctgcc   3039
ccccgcttca gtctctacca tatctggtcc catcatggac ttcctatttc ctggcatttt   3099
tgtccctttg gaagaagaaa taggactcag aatacagtgg catgagtgat tacactggca   3159
gcattatctc aggctcccta gaatctggag agcttaccaa catgtaaagc tgttcatttt   3219
tccaccgtgg gtcaccaatg ccagaaaacc agacatcacg gggaaagaat gttgcttact   3279
ttttaccagg agtgcagttc attttttca ccctgttttt gaagtcgtat tattcacttg    3339
taaaaatgat tgtaacagat aaaaaatgta tctgcagcaa ctctgcaggt ttgtgaaata   3399
ggatgaaact caatcttttt ctattgtggg tttgcatttg aaaagcaggt tgaatccttg   3459
ctctcttctc caaatttggt gtggtataaa gacacacaaa tcattttaac ttggacattt   3519
aaagatcagt cttagtgttt gttcagtcct gttacaaaat agataactga gcacctatcg   3579
cataacattt tgcggtggct tttagccatg ctggggttag atgtgtttga gagtcaaatg   3639
aaagctatgg atcttctcag caattaaaaa aaatgcatat attcacattc acagaaacat   3699
tggcagaacc cagttttaat ggtacagagg agtagtttat agtgttgatt tcaccaaaat   3759
cagagggctg aaagagacac ttctatagac tgcatcctga gcctagtgca gggcttgtct   3819
agctaatgtg ggcagccacc acccactgtg tatgaacaag tctgaagcaa gttggccttg   3879
cccttgagag tatatgggga ccagtcttca tgtcttggag taatttgtca aatgttaccc   3939
tttttgatca gggtgtaggg ggaggatatt gctagtatat tttcagtggt ttgtatgttc   3999
tctctgtcac tgacttattt gtaagagaaa attagttgga cttgtttatt ttctagtagc   4059
ttttataagt acactcaaga atttgtcagg gagaataatt ctgatagtgc atcccatact   4119
gcaaaagaat ttgtgtgtgt gtgtgtgtgt gtgtgtgtgt atgtgtatgt atacatatat   4179
atctctccat ataggtattt ctttgatact tgtaatttta aatttcagct tcacgatata   4239
aaataatata agaacttctg gtttacaaaa tgtaaaatct taagccaatg gaacccttga   4299
tttcctacct cagtgtacac tcaactattg gttgtatcag tttgtgtatg tgcaaatgtc   4359
aaataatctt ttgctttaat tgctactgta cttgctttga aagattacct actattttat   4419
gataaaatgt agttgtctcc agagcttaaa tataatttgt aaagcacttg gtttaaattt   4479
ctctctacct ataaacagtt tagcattaag ggtttctatt aatgacacag aattattggc   4539
caagtgtaat ttcttaaaat ttagcattac tttaaatagc cagcatgtaa tacaagtaac   4599
tacactacct catatctaca tgattttcaa gttgtaatgc agatggacag ataaaaaaga   4659
ttttacgttt gtcttttggc cataagtggg aaagttttct gtatattgca tagcattaca   4719
catttatgcc tattttaaca ttaacttcta aagaagtttt ttctaagaaa atgtttcaag   4779
gcaatatttt ttttgaggct gccgaagaca aatgacagga ttatgagtat acagtgtatg   4839
ccttttcctt catgcagaat tttgaaatgt tttcagtttg tatattgcat attcacatga   4899
tcattgctca ctattttatg aactggcctt ctcaatgttt gatgattttt taaaagctgt   4959
tatgttgaat tcagtaaaat aacattacct tattttttt cttattcaaa ttctggaact    5019
```

```
atagcaaata attcgttaaa ttgtcatatt caaaacaaat gtggatacag tcttggttct   5079

ccatctgtaa tttttttaa cagtttgcta tagcttactg cttaactaat tttaaataag    5139

gaaataagta tgttagatgc agtagacgat acaggttgca tgtggacact cagtcacatt   5199

aacaacttgg gaaaaaaatg gcaatgttac ggtgaattct caggtgaact tttttcagtt   5259

ataaaacatc tattttgaat ctgtaaatat tttaaatgtt ttattaaggc atgtaataaa   5319

ctattctttg aaacttgttg ggtagaatga aaattaaagc cataatggta aaagatggca   5379

tactgattat aaaagaagca gaaaaacatt gattttttta tatctttcat aatataattt   5439

tctaacaatg caataaaacc actaaacttt tgtgtc                             5475

<210> SEQ ID NO 2
<211> LENGTH: 736
<212> TYPE: PRT
<213> ORGANISM: Homo sapiens

<400> SEQUENCE: 2

Met Ser Leu Ser Glu Asn Ser Val Phe Ala Tyr Glu Ser Ser Val His
1               5                   10                  15

Ser Thr Asn Val Leu Leu Ser Leu Asn Asp Gln Arg Lys Lys Asp Val
            20                  25                  30

Leu Cys Asp Val Thr Ile Phe Val Glu Gly Gln Arg Phe Arg Ala His
        35                  40                  45

Arg Ser Val Leu Ala Ala Cys Ser Ser Tyr Phe His Ser Arg Ile Val
    50                  55                  60

Gly Gln Ala Asp Gly Glu Leu Asn Ile Thr Leu Pro Glu Glu Val Thr
65                  70                  75                  80

Val Lys Gly Phe Glu Pro Leu Ile Gln Phe Ala Tyr Thr Ala Lys Leu
                85                  90                  95

Ile Leu Ser Lys Glu Asn Val Asp Glu Val Cys Lys Cys Val Glu Phe
            100                 105                 110

Leu Ser Val His Asn Ile Glu Glu Ser Cys Phe Gln Phe Leu Lys Phe
        115                 120                 125

Lys Phe Leu Asp Ser Thr Ala Asp Gln Gln Glu Cys Pro Arg Lys Lys
    130                 135                 140

Cys Phe Ser Ser His Cys Gln Lys Thr Asp Leu Lys Leu Ser Leu Leu
145                 150                 155                 160

Asp Gln Arg Asp Leu Glu Thr Asp Glu Val Glu Glu Phe Leu Glu Asn
                165                 170                 175

Lys Asn Val Gln Thr Pro Gln Cys Lys Leu Arg Arg Tyr Gln Gly Asn
            180                 185                 190

Ala Lys Ala Ser Pro Pro Leu Gln Asp Ser Ala Ser Gln Thr Tyr Glu
        195                 200                 205

Ser Met Cys Leu Glu Lys Asp Ala Ala Leu Ala Leu Pro Ser Leu Cys
    210                 215                 220

Pro Lys Tyr Arg Lys Phe Gln Lys Ala Phe Gly Thr Asp Arg Val Arg
225                 230                 235                 240

Thr Gly Glu Ser Ser Val Lys Asp Ile His Ala Ser Val Gln Pro Asn
                245                 250                 255

Glu Arg Ser Glu Asn Glu Cys Leu Gly Gly Val Pro Glu Cys Arg Asp
            260                 265                 270

Leu Gln Val Met Leu Lys Cys Asp Glu Ser Lys Leu Ala Met Glu Pro
        275                 280                 285
```

-continued

```
Glu Glu Thr Lys Lys Asp Pro Ala Ser Gln Cys Pro Thr Glu Lys Ser
    290                 295                 300

Glu Val Thr Pro Phe Pro His Asn Ser Ser Ile Asp Pro His Gly Leu
305                 310                 315                 320

Tyr Ser Leu Ser Leu Leu His Thr Tyr Asp Gln Tyr Gly Asp Leu Asn
                325                 330                 335

Phe Ala Gly Met Gln Asn Thr Thr Val Leu Thr Glu Lys Pro Leu Ser
            340                 345                 350

Gly Thr Asp Val Gln Glu Lys Thr Phe Gly Glu Ser Gln Asp Leu Pro
        355                 360                 365

Leu Lys Ser Asp Leu Gly Thr Arg Glu Asp Ser Ser Val Ala Ser Ser
    370                 375                 380

Asp Arg Ser Ser Val Glu Arg Glu Val Ala Glu His Leu Ala Lys Gly
385                 390                 395                 400

Phe Trp Ser Asp Ile Cys Ser Thr Asp Thr Pro Cys Gln Met Gln Leu
                405                 410                 415

Ser Pro Ala Val Ala Lys Asp Gly Ser Glu Gln Ile Ser Gln Lys Arg
            420                 425                 430

Ser Glu Cys Pro Trp Leu Gly Ile Arg Ile Ser Glu Ser Pro Glu Pro
        435                 440                 445

Gly Gln Arg Thr Phe Thr Thr Leu Ser Ser Val Asn Cys Pro Phe Ile
    450                 455                 460

Ser Thr Leu Ser Thr Glu Gly Cys Ser Ser Asn Leu Glu Ile Gly Asn
465                 470                 475                 480

Asp Asp Tyr Val Ser Glu Pro Gln Gln Glu Pro Cys Pro Tyr Ala Cys
                485                 490                 495

Val Ile Ser Leu Gly Asp Asp Ser Glu Thr Asp Thr Glu Gly Asp Ser
            500                 505                 510

Glu Ser Cys Ser Ala Arg Glu Gln Glu Cys Glu Val Lys Leu Pro Phe
        515                 520                 525

Asn Ala Gln Arg Ile Ile Ser Leu Ser Arg Asn Asp Phe Gln Ser Leu
    530                 535                 540

Leu Lys Met His Lys Leu Thr Pro Glu Gln Leu Asp Cys Ile His Asp
545                 550                 555                 560

Ile Arg Arg Arg Ser Lys Asn Arg Ile Ala Ala Gln Arg Cys Arg Lys
                565                 570                 575

Arg Lys Leu Asp Cys Ile Gln Asn Leu Glu Ser Glu Ile Glu Lys Leu
            580                 585                 590

Gln Ser Glu Lys Glu Ser Leu Leu Lys Glu Arg Asp His Ile Leu Ser
        595                 600                 605

Thr Leu Gly Glu Thr Lys Gln Asn Leu Thr Gly Leu Cys Gln Lys Val
    610                 615                 620

Cys Lys Glu Ala Ala Leu Ser Gln Glu Gln Ile Gln Ile Leu Ala Lys
625                 630                 635                 640

Tyr Ser Ala Ala Asp Cys Pro Leu Ser Phe Leu Ile Ser Glu Lys Asp
                645                 650                 655

Lys Ser Thr Pro Asp Gly Glu Leu Ala Leu Pro Ser Ile Phe Ser Leu
            660                 665                 670

Ser Asp Arg Pro Pro Ala Val Leu Pro Pro Cys Ala Arg Gly Asn Ser
        675                 680                 685

Glu Pro Gly Tyr Ala Arg Gly Gln Glu Ser Gln Gln Met Ser Thr Ala
    690                 695                 700

Thr Ser Glu Gln Ala Gly Pro Ala Glu Gln Cys Arg Gln Ser Gly Gly
```

```
705                 710                 715                 720

Ile Ser Asp Phe Cys Gln Gln Met Thr Asp Lys Cys Thr Thr Asp Glu
                725                 730                 735


<210> SEQ ID NO 3
<211> LENGTH: 3373
<212> TYPE: DNA
<213> ORGANISM: Homo sapiens
<220> FEATURE:
<221> NAME/KEY: CDS
<222> LOCATION: (142)..(1560)

<400> SEQUENCE: 3

ctcttcgccc gggtggcgtt gggcccgcgc gggcgctcgg gtgactgcag ctgctcagct      60

cccctccccc gccccgcgcc gcgcggccgc ccgtcgcttc gcacagggct ggatggttgt     120

attgggcagg gtggctccag g atg tta gga act gtg aag atg gaa ggg cat       171
                        Met Leu Gly Thr Val Lys Met Glu Gly His
                        1               5                   10

gaa acc agc gac tgg aac agc tac tac gca gac acg cag gag gcc tac       219
Glu Thr Ser Asp Trp Asn Ser Tyr Tyr Ala Asp Thr Gln Glu Ala Tyr
                15                  20                  25

tcc tcc gtc ccg gtc agc aac atg aac tca ggc ctg ggc tcc atg aac       267
Ser Ser Val Pro Val Ser Asn Met Asn Ser Gly Leu Gly Ser Met Asn
            30                  35                  40

tcc atg aac acc tac atg acc atg aac acc atg act acg agc ggc aac       315
Ser Met Asn Thr Tyr Met Thr Met Asn Thr Met Thr Thr Ser Gly Asn
        45                  50                  55

atg acc ccg gcg tcc ttc aac atg tcc tat gcc aac ccg ggc cta ggg       363
Met Thr Pro Ala Ser Phe Asn Met Ser Tyr Ala Asn Pro Gly Leu Gly
    60                  65                  70

gcc ggc ctg agt ccc ggc gca gta gcc ggc atg ccg ggg ggc tcg gcg       411
Ala Gly Leu Ser Pro Gly Ala Val Ala Gly Met Pro Gly Gly Ser Ala
75                  80                  85                  90

ggc gcc atg aac agc atg act gcg gcc ggc gtg acg gcc atg ggt acg       459
Gly Ala Met Asn Ser Met Thr Ala Ala Gly Val Thr Ala Met Gly Thr
                95                  100                 105

gcg ctg agc ccg agc ggc atg ggc gcc atg ggt gcg cag cag gcg gcc       507
Ala Leu Ser Pro Ser Gly Met Gly Ala Met Gly Ala Gln Gln Ala Ala
            110                 115                 120

tcc atg aat ggc ctg ggc ccc tac gcg gcc gcc atg aac ccg tgc atg       555
Ser Met Asn Gly Leu Gly Pro Tyr Ala Ala Ala Met Asn Pro Cys Met
        125                 130                 135

agc ccc atg gcg tac gcg ccg tcc aac ctg ggc cgc agc cgc gcg ggc       603
Ser Pro Met Ala Tyr Ala Pro Ser Asn Leu Gly Arg Ser Arg Ala Gly
    140                 145                 150

ggc ggc ggc gac gcc aag acg ttc aag cgc agc tac ccg cac gcc aag       651
Gly Gly Gly Asp Ala Lys Thr Phe Lys Arg Ser Tyr Pro His Ala Lys
155                 160                 165                 170

ccg ccc tac tcg tac atc tcg ctc atc acc atg gcc atc cag cag gcg       699
Pro Pro Tyr Ser Tyr Ile Ser Leu Ile Thr Met Ala Ile Gln Gln Ala
                175                 180                 185

ccc agc aag atg ctc acg ctg agc gag atc tac cag tgg atc atg gac       747
Pro Ser Lys Met Leu Thr Leu Ser Glu Ile Tyr Gln Trp Ile Met Asp
            190                 195                 200

ctc ttc ccc tat tac cgg cag aac cag cag cgc tgg cag aac tcc atc       795
Leu Phe Pro Tyr Tyr Arg Gln Asn Gln Gln Arg Trp Gln Asn Ser Ile
        205                 210                 215

cgc cac tcg ctg tcc ttc aat gac tgc ttc gtc aag gtg gca cgc tcc       843
Arg His Ser Leu Ser Phe Asn Asp Cys Phe Val Lys Val Ala Arg Ser
    220                 225                 230
```

-continued

```
ccg gac aag ccg ggc aag ggc tcc tac tgg acg ctg cac ccg gac tcc      891
Pro Asp Lys Pro Gly Lys Gly Ser Tyr Trp Thr Leu His Pro Asp Ser
235                 240                 245                 250

ggc aac atg ttc gag aac ggc tgc tac ttg cgc cgc cag aag cgc ttc      939
Gly Asn Met Phe Glu Asn Gly Cys Tyr Leu Arg Arg Gln Lys Arg Phe
                255                 260                 265

aag tgc gag aag cag ccg ggg gcc ggc ggc ggg ggc ggg agc gga agc      987
Lys Cys Glu Lys Gln Pro Gly Ala Gly Gly Gly Gly Gly Ser Gly Ser
            270                 275                 280

ggg ggc agc ggc gcc aag ggc ggc cct gag agc cgc aag gac ccc tct     1035
Gly Gly Ser Gly Ala Lys Gly Gly Pro Glu Ser Arg Lys Asp Pro Ser
        285                 290                 295

ggc gcc tct aac ccc agc gcc gac tcg ccc ctc cat cgg ggt gtg cac     1083
Gly Ala Ser Asn Pro Ser Ala Asp Ser Pro Leu His Arg Gly Val His
    300                 305                 310

ggg aag acc ggc cag cta gag ggc gcg ccg gcc ccc ggg ccc gcc gcc     1131
Gly Lys Thr Gly Gln Leu Glu Gly Ala Pro Ala Pro Gly Pro Ala Ala
315                 320                 325                 330

agc ccc cag act ctg gac cac agt ggg gcg acg gcg aca ggg ggc gcc     1179
Ser Pro Gln Thr Leu Asp His Ser Gly Ala Thr Ala Thr Gly Gly Ala
                335                 340                 345

tcg gag ttg aag act cca gcc tcc tca act gcg ccc ccc ata agc tcc     1227
Ser Glu Leu Lys Thr Pro Ala Ser Ser Thr Ala Pro Pro Ile Ser Ser
            350                 355                 360

ggg ccc ggg gcg ctg gcc tct gtg ccc gcc tct cac ccg gca cac ggc     1275
Gly Pro Gly Ala Leu Ala Ser Val Pro Ala Ser His Pro Ala His Gly
        365                 370                 375

ttg gca ccc cac gag tcc cag ctg cac ctg aaa ggg gac ccc cac tac     1323
Leu Ala Pro His Glu Ser Gln Leu His Leu Lys Gly Asp Pro His Tyr
    380                 385                 390

tcc ttc aac cac ccg ttc tcc atc aac aac ctc atg tcc tcc tcg gag     1371
Ser Phe Asn His Pro Phe Ser Ile Asn Asn Leu Met Ser Ser Ser Glu
395                 400                 405                 410

cag cag cat aag ctg gac ttc aag gca tac gaa cag gca ctg caa tac     1419
Gln Gln His Lys Leu Asp Phe Lys Ala Tyr Glu Gln Ala Leu Gln Tyr
                415                 420                 425

tcg cct tac ggc tct acg ttg ccc gcc agc ctg cct cta ggc agc gcc     1467
Ser Pro Tyr Gly Ser Thr Leu Pro Ala Ser Leu Pro Leu Gly Ser Ala
            430                 435                 440

tcg gtg acc acc agg agc ccc atc gag ccc tca gcc ctg gag ccg gcg     1515
Ser Val Thr Thr Arg Ser Pro Ile Glu Pro Ser Ala Leu Glu Pro Ala
        445                 450                 455

tac tac caa ggt gtg tat tcc aga ccc gtc cta aac act tcc tag         1560
Tyr Tyr Gln Gly Val Tyr Ser Arg Pro Val Leu Asn Thr Ser
    460                 465                 470

ctcccgggac tggggggttt gtctggcata gccatgctgg tagcaagaga gaaaaaatca   1620

acagcaaaca aaaccacaca aaccaaaccg tcaacagcat aataaaatcc caacaactat   1680

ttttatttca tttttcatgc acaacctttc ccccagtgca aaagactgtt actttattat   1740

tgtattcaaa attcattgtg tatattacta caaagacaac cccaaaccaa tttttttcct   1800

gcgaagttta atgatccaca agtgtatata tgaaattctc ctccttcctt gcccccctct   1860

ctttcttccc tctttcccct ccagacattc tagtttgtgg agggttattt aaaaaaacaa   1920

aaaaggaaga tggtcaagtt tgtaaaatat ttgtttgtgc tttttccccc tccttacctg   1980

accccctacg agtttacagg tctgtggcaa tactcttaac cataagaatt gaaatggtga   2040

agaaacaagt atacactaga ggctcttaaa agtattgaaa gacaatactg ctgttatata   2100
```

-continued

```
gcaagacata aacagattat aaacatcaga gccatttgct tctcagttta catttctgat   2160

acatgcagat agcagatgtc tttaaatgaa atacatgtat attgtgtatg gacttaatta   2220

tgcacatgct cagatgtgta gacatcctcc gtatatttac ataacatata gaggtaatag   2280

ataggtgata tacatgatac attctcaaga gttgcttgac cgaaagttac aaggacccca   2340

accccttttgt cctctctacc cacagatggc cctgggaatc aattcctcag gaattgccct  2400

caagaactct gcttcttgct ttgcagagtg ccatggtcat gtcattctga ggtcacataa   2460

cacataaaat tagtttctat gagtgtatac catttaaaga atttttttt cagtaaaagg    2520

gaatattaca atgttggagg agagataagt tatagggagc tggatttcaa aacgtggtcc   2580

aagattcaaa aatcctattg atagtggcca ttttaatcat tgccatcgtg tgcttgtttc   2640

atccagtgtt atgcactttc cacagttgga catggtgtta gtatagccag acgggtttca   2700

ttattatttc tctttgcttt ctcaatgtta atttattgca tggtttattc tttttcttta   2760

cagctgaaat tgctttaaat gatggttaaa attacaaatt aaattgttaa tttttatcaa   2820

tgtgattgta attaaaaata ttttgattta aataacaaaa ataataccag attttaagcc   2880

gtggaaaatg ttcttgatca tttgcagtta aggactttaa ataaatcaaa tgttaacaaa   2940

agagcatttc tgttattttt tttcacttaa ctaaatccga agtgaatatt tctgaatacg   3000

atatttttca aattctagaa ctgaatataa atgacaaaaa tgaaaataaa attgttttgt   3060

ctgttgttat aatgaatgtg tagctagtaa aaaggagtga aagaaattca agtaaagtgt   3120

ataagttgat ttaatattcc aagagttgag atttttaaga ttctttattc ccagtgatgt   3180

ttacttcatt tttttttttt tttttgacac cggcttaagc cttctgtgtt tcctttgagc   3240

cttttcacta caaaatcaaa tattaattta actacctttc ctccttcccc aatgtatcac   3300

ttttctttat ctgagaattc ttccaatgaa aataaaatat cagctgtggc tgatagaatt   3360

aagttgtgtc caa                                                      3373
```

```
<210> SEQ ID NO 4
<211> LENGTH: 472
<212> TYPE: PRT
<213> ORGANISM: Homo sapiens

<400> SEQUENCE: 4

Met Leu Gly Thr Val Lys Met Glu Gly His Glu Thr Ser Asp Trp Asn
1               5                   10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Pro Gly Leu Gly Ala Gly Leu Ser Pro Gly
65                  70                  75                  80

Ala Val Ala Gly Met Pro Gly Gly Ser Ala Gly Ala Met Asn Ser Met
                85                  90                  95

Thr Ala Ala Gly Val Thr Ala Met Gly Thr Ala Leu Ser Pro Ser Gly
            100                 105                 110

Met Gly Ala Met Gly Ala Gln Gln Ala Ala Ser Met Asn Gly Leu Gly
        115                 120                 125

Pro Tyr Ala Ala Ala Met Asn Pro Cys Met Ser Pro Met Ala Tyr Ala
    130                 135                 140
```

```
Pro Ser Asn Leu Gly Arg Ser Arg Ala Gly Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
225                 230                 235                 240

Gly Ser Tyr Trp Thr Leu His Pro Asp Ser Gly Asn Met Phe Glu Asn
                245                 250                 255

Gly Cys Tyr Leu Arg Arg Gln Lys Arg Phe Lys Cys Glu Lys Gln Pro
            260                 265                 270

Gly Ala Gly Gly Gly Gly Gly Ser Gly Ser Gly Gly Ser Gly Ala Lys
        275                 280                 285

Gly Gly Pro Glu Ser Arg Lys Asp Pro Ser Gly Ala Ser Asn Pro Ser
    290                 295                 300

Ala Asp Ser Pro Leu His Arg Gly Val His Gly Lys Thr Gly Gln Leu
305                 310                 315                 320

Glu Gly Ala Pro Ala Pro Gly Pro Ala Ala Ser Pro Gln Thr Leu Asp
                325                 330                 335

His Ser Gly Ala Thr Ala Thr Gly Gly Ala Ser Glu Leu Lys Thr Pro
            340                 345                 350

Ala Ser Ser Thr Ala Pro Pro Ile Ser Ser Gly Pro Gly Ala Leu Ala
        355                 360                 365

Ser Val Pro Ala Ser His Pro Ala His Gly Leu Ala Pro His Glu Ser
    370                 375                 380

Gln Leu His Leu Lys Gly Asp Pro His Tyr Ser Phe Asn His Pro Phe
385                 390                 395                 400

Ser Ile Asn Asn Leu Met Ser Ser Ser Glu Gln Gln His Lys Leu Asp
                405                 410                 415

Phe Lys Ala Tyr Glu Gln Ala Leu Gln Tyr Ser Pro Tyr Gly Ser Thr
            420                 425                 430

Leu Pro Ala Ser Leu Pro Leu Gly Ser Ala Ser Val Thr Thr Arg Ser
        435                 440                 445

Pro Ile Glu Pro Ser Ala Leu Glu Pro Ala Tyr Tyr Gln Gly Val Tyr
    450                 455                 460

Ser Arg Pro Val Leu Asn Thr Ser
465                 470

<210> SEQ ID NO 5
<211> LENGTH: 25
<212> TYPE: RNA
<213> ORGANISM: Artificial Sequence
<220> FEATURE:
<223> OTHER INFORMATION: siRNA BACH1-1

<400> SEQUENCE: 5

ggucaaagga cuuucacaac auuaa                                        25


<210> SEQ ID NO 6
<211> LENGTH: 25
<212> TYPE: RNA
```

<213> ORGANISM: Artificial Sequence
<220> FEATURE:
<223> OTHER INFORMATION: siRNA BACH1-2

<400> SEQUENCE: 6
gggcaccagg gaagauagua guguu 25

<210> SEQ ID NO 7
<211> LENGTH: 20
<212> TYPE: DNA
<213> ORGANISM: Artificial Sequence
<220> FEATURE:
<223> OTHER INFORMATION: ACTB primer forward

<400> SEQUENCE: 7
atttgcggtg gacgatggag 20

<210> SEQ ID NO 8
<211> LENGTH: 20
<212> TYPE: DNA
<213> ORGANISM: Artificial Sequence
<220> FEATURE:
<223> OTHER INFORMATION: ACTB primer reverse

<400> SEQUENCE: 8
agagatggcc acggctgctt 20

<210> SEQ ID NO 9
<211> LENGTH: 20
<212> TYPE: DNA
<213> ORGANISM: Artificial Sequence
<220> FEATURE:
<223> OTHER INFORMATION: BACH1 primer forward

<400> SEQUENCE: 9
aatcgtaggc caggctgatg 20

<210> SEQ ID NO 10
<211> LENGTH: 20
<212> TYPE: DNA
<213> ORGANISM: Artificial Sequence
<220> FEATURE:
<223> OTHER INFORMATION: BACH1 primer reverse

<400> SEQUENCE: 10
agcagtgtag gcaaactgaa 20

<210> SEQ ID NO 11
<211> LENGTH: 20
<212> TYPE: DNA
<213> ORGANISM: Artificial Sequence
<220> FEATURE:
<223> OTHER INFORMATION: CDH1 primer forward

<400> SEQUENCE: 11
tcctggcctc agaagacaga 20

<210> SEQ ID NO 12
<211> LENGTH: 20
<212> TYPE: DNA
<213> ORGANISM: Artificial Sequence
<220> FEATURE:
<223> OTHER INFORMATION: CDH1 primer reverse

<400> SEQUENCE: 12
ccttggccag tgatgctgta 20

<210> SEQ ID NO 13
<211> LENGTH: 20
<212> TYPE: DNA
<213> ORGANISM: Artificial Sequence
<220> FEATURE:
<223> OTHER INFORMATION: OCLN primer forward

<400> SEQUENCE: 13
gagttgacag tcccatggca 20

<210> SEQ ID NO 14
<211> LENGTH: 20
<212> TYPE: DNA
<213> ORGANISM: Artificial Sequence
<220> FEATURE:
<223> OTHER INFORMATION: OCLN primer reverse

<400> SEQUENCE: 14
ctgaagtcat ccacaggcga 20

<210> SEQ ID NO 15
<211> LENGTH: 20
<212> TYPE: DNA
<213> ORGANISM: Artificial Sequence
<220> FEATURE:
<223> OTHER INFORMATION: FOXA1 primer forward

<400> SEQUENCE: 15
ggtggctcca ggatgttagg 20

<210> SEQ ID NO 16
<211> LENGTH: 20
<212> TYPE: DNA
<213> ORGANISM: Artificial Sequence
<220> FEATURE:
<223> OTHER INFORMATION: FOXA1 primer reverse

<400> SEQUENCE: 16
cccaggcctg agttcatgtt 20

<210> SEQ ID NO 17
<211> LENGTH: 20
<212> TYPE: DNA
<213> ORGANISM: Artificial Sequence
<220> FEATURE:
<223> OTHER INFORMATION: VIM primer forward

<400> SEQUENCE: 17
ggaccagcta accaacgaca 20

<210> SEQ ID NO 18
<211> LENGTH: 20
<212> TYPE: DNA
<213> ORGANISM: Artificial Sequence
<220> FEATURE:
<223> OTHER INFORMATION: VIM primer reverse

<400> SEQUENCE: 18
gggtgttttc ggcttcctct 20

<210> SEQ ID NO 19
<211> LENGTH: 20
<212> TYPE: DNA
<213> ORGANISM: Artificial Sequence
<220> FEATURE:

<223> OTHER INFORMATION: SNAI2 primer forward

<400> SEQUENCE: 19
caacgcctcc aaaaagccaa 20

<210> SEQ ID NO 20
<211> LENGTH: 20
<212> TYPE: DNA
<213> ORGANISM: Artificial Sequence
<220> FEATURE:
<223> OTHER INFORMATION: SNAI2 primer reverse

<400> SEQUENCE: 20
acagtgatgg ggctgtatgc 20

<210> SEQ ID NO 21
<211> LENGTH: 23
<212> TYPE: RNA
<213> ORGANISM: Artificial Sequence
<220> FEATURE:
<223> OTHER INFORMATION: guide RNA BACH1-1

<400> SEQUENCE: 21
ccgcgcucac cgguccgugc ugg 23

<210> SEQ ID NO 22
<211> LENGTH: 23
<212> TYPE: RNA
<213> ORGANISM: Artificial Sequence
<220> FEATURE:
<223> OTHER INFORMATION: guide RNA BACH1-2

<400> SEQUENCE: 22
ccacucaaga aucguaggcc agg 23

<210> SEQ ID NO 23
<211> LENGTH: 65
<212> TYPE: DNA
<213> ORGANISM: Artificial Sequence
<220> FEATURE:
<223> OTHER INFORMATION: hg19

<400> SEQUENCE: 23
ccgcgctcac cggtccgtgc tggcggcatg cagcagttac ttccactcaa gaatcgtagg 60
ccagg 65

<210> SEQ ID NO 24
<211> LENGTH: 52
<212> TYPE: DNA
<213> ORGANISM: Artificial Sequence
<220> FEATURE:
<223> OTHER INFORMATION: sgBACH1-1

<400> SEQUENCE: 24
ccgcgctcac cggcatgcag cagttacttc cactcaagaa tcgtaggcca gg 52

-continued

```
<210> SEQ ID NO 25
<211> LENGTH: 66
<212> TYPE: DNA
<213> ORGANISM: Artificial Sequence
<220> FEATURE:
<223> OTHER INFORMATION: sgBACH1-2

<400> SEQUENCE: 25

ccgcgctcac cggtccgtgc tggcggcatg cagcagttac ttccactcaa agaatcgtag     60

gccagg                                                                66
```